(12) United States Patent
Kirsch et al.

(10) Patent No.: US 10,344,217 B2
(45) Date of Patent: Jul. 9, 2019

(54) DEVICE FOR CONTROLLING THE PASSAGE OF ENERGY, CONTAINING A DICHROIC DYE COMPOUND

(71) Applicant: MERCK PATENT GMBH, Darmstadt (DE)

(72) Inventors: Peer Kirsch, Seeheim-Jugenheim (DE); Alexander Hahn, Biebesheim (DE); Andreas Ruhl, Rossdorf (DE); Susann Beck, Darmstadt (DE); Junyou Pan, Frankfurt am Main (DE); Michael Junge, Pfungstadt (DE); Andreas Beyer, Hanau (DE); Ursula Patwal, Reinheim (DE)

(73) Assignee: MERCK PATENT GMBH, Darmstadt (DE)

(*) Notice: Subject to any disclaimer, the term of this patent is extended or adjusted under 35 U.S.C. 154(b) by 0 days.

(21) Appl. No.: 14/893,618

(22) PCT Filed: Apr. 29, 2014

(86) PCT No.: PCT/EP2014/001149
§ 371 (c)(1),
(2) Date: Nov. 24, 2015

(87) PCT Pub. No.: WO2014/187529
PCT Pub. Date: Nov. 27, 2014

(65) Prior Publication Data
US 2016/0108317 A1  Apr. 21, 2016

(30) Foreign Application Priority Data

May 24, 2013 (EP) .................................. 13002711

(51) Int. Cl.
*H01L 51/00* (2006.01)
*C07C 255/55* (2006.01)
*C07C 69/74* (2006.01)
*G02F 1/139* (2006.01)
*C09K 19/60* (2006.01)
*C09B 57/00* (2006.01)
*C09B 23/10* (2006.01)
*C09B 69/00* (2006.01)
*C07D 285/14* (2006.01)
*C07D 417/04* (2006.01)
*C07D 417/14* (2006.01)
*C07D 495/04* (2006.01)
*C09K 19/30* (2006.01)

(52) U.S. Cl.
CPC .......... *C09K 19/60* (2013.01); *C07D 285/14* (2013.01); *C07D 417/04* (2013.01); *C07D 417/14* (2013.01); *C07D 495/04* (2013.01); *C09B 23/105* (2013.01); *C09B 57/00* (2013.01); *C09B 69/008* (2013.01); *H01L 51/0068* (2013.01); *H01L 51/0071* (2013.01); *H01L 51/0074* (2013.01); *C09K 2019/3009* (2013.01); *C09K 2019/3016* (2013.01); *C09K 2019/3019* (2013.01); *C09K 2019/3021* (2013.01); *C09K 2019/3078* (2013.01); *C09K 2219/13* (2013.01)

(58) Field of Classification Search
CPC ...... C09K 19/60; C09B 57/00; C07D 417/14; C07D 285/14; C07D 417/04; C07D 495/04; H01L 51/0074; H01L 51/0068; H01L 51/0071
USPC ................ 136/252; 252/299.1, 586; 257/40, 257/E51.049, E51.05; 313/504, 506; 428/690, 917; 548/126, 134
See application file for complete search history.

(56) References Cited

U.S. PATENT DOCUMENTS

| | | | |
|---|---|---|---|
| 7,223,484 B2 | 5/2007 | Stossel et al. | |
| 8,383,761 B2 | 2/2013 | Beaujuge et al. | |
| 8,604,158 B2 | 12/2013 | Beaujuge et al. | |
| 2004/0136066 A1* | 7/2004 | Kashima | G02B 5/3016 359/487.04 |
| 2006/0052612 A1* | 3/2006 | Stossel | C07D 285/14 548/126 |
| 2010/0298527 A1 | 11/2010 | Beaujuge et al. | |
| 2013/0231456 A1 | 9/2013 | Beaujuge et al. | |
| 2014/0221663 A1 | 8/2014 | Schimperna et al. | |
| 2014/0303379 A1 | 10/2014 | Santarelli et al. | |

FOREIGN PATENT DOCUMENTS

| | | | | |
|---|---|---|---|---|
| CN | 1671675 A | | 9/2005 | |
| CN | 101842410 A | | 9/2010 | |
| DE | 19957193 A1 | * | 6/2000 | ........... C07D 239/26 |
| JP | 2003-104976 | * | 4/2003 | ........... C07D 285/10 |
| JP | 2003104976 A | | 4/2003 | |
| WO | 2004002970 A1 | | 1/2004 | |
| WO | 2009058877 A1 | | 5/2009 | |

(Continued)

OTHER PUBLICATIONS

Qian Liu, Ming Wang, Cuihong Li, Enquan Jin, Chun Du, Jianjun Zhou, * Lin Li, Zhishan Bo, Polymer Photovoltaic Cells Based on Polymethacrylate Bearing Semiconducting Side Chains, Macromol. Rapid Commun. 2012, 33, 2097-2102.*

(Continued)

*Primary Examiner* — Bijan Ahvazi

(74) *Attorney, Agent, or Firm* — Millen White Zelano & Branigan, PC

(57) ABSTRACT

The present application relates to a device for regulating the passage of energy from an outside space into an inside space, where the device comprises a switching layer comprising one or more dichroic dyes of a formula (I) or formula (II).

24 Claims, No Drawings

(56) References Cited

FOREIGN PATENT DOCUMENTS

| WO | WO 2011/154077 A1 | * | 12/2011 |
| WO | 2013005177 A2 | | 1/2013 |
| WO | 2013021315 A1 | | 2/2013 |
| WO | 2013/097919 A1 | | 7/2013 |

OTHER PUBLICATIONS

Zhihua Chen et al. Benzo[d][1,2,3]thiadiazole (isoBT): Synthesis, Structural Analysis, and Implementation in Semiconducting Polymers,Chem. Mater. 2016, 28, 6390-6400, © 2016 American Chemical Society.*
Office Action for related Chinese Patent Application No. 201480029535 dated Sep. 30, 2016.
International Search Report for PCT/EP2014/001149 dated Jul. 29, 2014.
Zhang, X. et al., "Highly dichroic benzo-2, 1, 3-thiadiazole dyes containing five linearly pi-conjugated aromatic residues, with fluorescent emission ranging from green to red, in a liquid crystal guest host system," Journal of Materials Chemistry, Feb. 2006, vol. 16, No. 8, pp. 736-740.
English Abstract for JP2003104976, Publication Date: Apr. 9, 2003.
Translation of Office Action corresponding to TW Patent Application No. 103118164, dated Jan. 19, 2018.
Translated summary of Office Action corresponding to TW (ROC) Patent Application No. 103118164, dated Jun. 19, 2018. (pp. 1-8).
Translated summary of Office Action corresponding to CN Patent Application No. 103118164, dated Jun. 19, 2018. (pp. 1-8).
Translated summary of Office Action corresponding to JP Patent Application No. 2016-514288, dated Mar. 9, 2018.
Yamaguchi, R., et al., Sensitization Effects of Fluorescent Dichroic Dyes in a Nematic Liquid Crystal and Fluorescence Colors, Mol. Crystl. Liq. Cryst., 2005, vol. 433, pp. 87-95.
Office Action in the corresponding European application dated 14721765.7 dated Jul. 27, 2018.

* cited by examiner

DEVICE FOR CONTROLLING THE PASSAGE OF ENERGY, CONTAINING A DICHROIC DYE COMPOUND

The present application relates to a device for regulating the passage of energy from an outside space into an inside space, where the device comprises a switching layer comprising one or more dichroic dyes of a formula (I) or formula (II).

A device for regulating the passage of energy is in the present application generally taken to mean a device which regulates the passage of energy through an area which has relatively high energy transmissivity. This area of relatively high energy transmissivity is preferably arranged within a structure of relatively lower energy transmissivity. For example, the area of high energy transmissivity can be a glass area or an open area, and the structure of lower energy transmissivity which contains the area of high energy transmissivity may be a wall.

The device preferably regulates the passage of energy from insolation, either directly or indirectly.

The regulated passage of energy takes place from an outside space, preferably the environment exposed directly to insolation, into an inside space, for example a building or a vehicle, or another unit which is substantially sealed off from the environment.

For the purposes of the present invention, the term energy is taken to mean, in particular, energy by electromagnetic radiation in the UV-A, VIS and NIR region. In particular, it is taken to mean energy by radiation which is not absorbed or is only absorbed to a negligible extent by the materials usually used in windows (for example glass). According to the definitions usually used, the UV-A region is taken to mean a wavelength of 320 to 380 nm, the VIS region is taken to mean a wavelength of 380 nm to 780 nm and the NIR region is taken to mean a wavelength of 780 nm to 2000 nm. Correspondingly, the term light is generally taken to mean electromagnetic radiation having wavelengths between 320 and 2000 nm.

For the purposes of the present application, a dichroic dye is taken to mean a light-absorbent compound in which the absorption properties are dependent on the alignment of the compound to the direction of polarisation of the light. A dichroic dye compound in accordance with the present application typically has an elongated shape, i.e. the compound is significantly longer in one spatial direction (longitudinal direction) than in the other two spatial directions.

In the area of devices for regulating the passage of energy from an outside space into an inside space, a number of different technical solutions have been proposed in past years.

An advantageous solution is the use of switching layers comprising a liquid-crystalline medium in combination with one or more dichroic dyes. By application of a voltage, a change in the spatial alignment of the molecules of the dichroic compound can be achieved in these switching layers, causing a change in their absorption and thus the transmission through the switching layer. A corresponding device is described, for example, in WO 2009/141295.

Alternatively, a change in transmission of this type can also be achieved without electrical voltage by a temperature-induced transition from an isotropic state of the liquid-crystalline medium to a liquid-crystalline state, as described, for example, in US 2010/0259698.

It is furthermore known to design devices comprising a switching layer comprising a liquid-crystalline medium comprising at least one dichroic dye in such a way that the energy absorbed by the dye is partly re-emitted as fluorescence radiation, which is itself conducted to a solar cell, which converts it into electrical energy (WO 2009/141295).

Rylene dyes have been described for use in the said devices, for example in WO 2009/141295, WO 2013/004677 and the as yet unpublished EP 12008320.9.

Furthermore, benzothiadiazole compounds are already generally known for a very wide variety of uses, for example in ChemPhysChem 2012, 13, 597 ff. for use as organic semiconductors, in Chem. Eur. J. 2008, 14, 11231 ff. for use as OLED materials, in J. Am. Chem. Soc. 1995, 117, 6791 ff. for use as constituents of polymers or in J. Mater. Chem. 2006, 16 736 ff. for use in guest-host liquid-crystal systems.

In the case of the above-mentioned devices for regulating the passage of energy, there is considerable interest in the development of improved devices, in particular with respect to the lifetime and the switching range (i.e. the difference in transmission in the bright state to the dark state). Furthermore, there is potential for improvement with respect to the energy yield in the case of devices which utilise the fluorescence emission of the dyes for recovery of energy by means of a solar cell. In the optimum case, the energy provided by the solar cell should be sufficient in order to provide all the energy necessary for operation of the device, or even exceed this amount.

In this connection, there is considerable interest in the development of alternative dichroic dyes, preferably those having at least one, particularly preferably several, of the following properties: good solubility in the liquid-crystalline medium, good light stability and high anisotropy of the absorption. In addition, the dyes should have strong light absorption in the VIS and/or NIR region of light. For the above-mentioned devices which convert emitted fluorescence light into electrical energy, it is furthermore of considerable interest for the compounds to have a high fluorescence quantum yield, high relative fluorescence from wave guidance and a high Stokes shift.

In the course of investigations on dye compounds, it has now been found, surprisingly, that one or more of the above-mentioned technical objects are achieved by a device comprising one or more dichroic dyes of a formula (I) or formula (II).

The present invention thus relates to a device for regulating the passage of energy from an outside space into an inside space, where the device comprises a switching layer comprising one or more dichroic dyes of a formula (I)

formula (I)

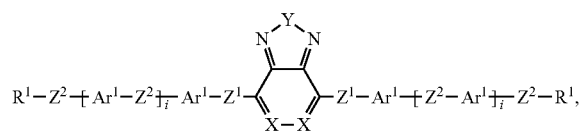

or a formula (II)

formula (II)

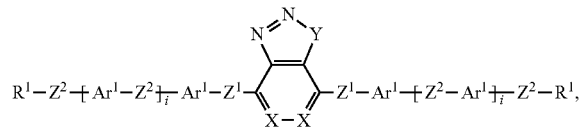

where:

$X$ is on each occurrence, identically or differently, $CR^2$ or N;

$Y$ is equal to S or Se;

$Z^1$ is on each occurrence, identically or differently, a single bond, $-CR^3=CR^3-$ or $-C\equiv C-$; or two, three, four or five groups combined with one another, selected from the groups $-CR^3=CR^3-$ and $-C\equiv C-$;

$Z^2$ is on each occurrence, identically or differently, a single bond, O, S, $C(R^3)_2$, $-CR^3=CR^3-$ or $-C\equiv C-$; or two, three, four or five groups combined with one another, selected from the groups O, S, $C(R^3)_2$, $-CR^3=CR^3-$ and $-C\equiv C-$;

$Ar^1$ is on each occurrence, identically or differently, an aryl or heteroaryl group having 5 to 30 aromatic ring atoms, which may be substituted by one or more radicals $R^4$;

$R^1$ is on each occurrence, identically or differently, H, D, F, CN, $N(R^5)_2$, or an alkyl, alkoxy or thioalkoxy group having 1 to 10 C atoms, which may be substituted by one or more radicals $R^5$, where one or more $CH_2$ groups in the alkyl, alkoxy or thioalkoxy groups may be replaced by $-R^5C=CR^5-$, $-C\equiv C-$, C=O, C=S, $-C(=O)O-$, $-OC(=O)-$, $Si(R^5)_2$, $NR^5$, $-O-$ or $-S-$;

$R^2$ is on each occurrence, identically or differently, H, D, F, Cl, CN, $-(C=O)OR^5$, $-O(C=O)R^5$, or an alkyl, alkoxy or thioalkoxy group having 1 to 10 C atoms, which may be substituted by one or more radicals $R^5$, where one or more $CH_2$ groups in the alkyl, alkoxy or thioalkoxy groups may be replaced by $-R^5C=CR^5-$, $-C\equiv C-$, C=O, C=S, $-C(=O)O-$, $-OC(=O)-$, $Si(R^5)_2$, $NR^5$, $-O-$ or $-S-$;

$R^3$, $R^4$ are on each occurrence, identically or differently, H, D, F, Cl, CN, or an alkyl, alkoxy or thioalkoxy group having 1 to 10 C atoms, which may be substituted by one or more radicals $R^5$, where one or more $CH_2$ groups in the alkyl, alkoxy or thioalkoxy groups may be replaced by $-R^5C=CR^5-$, $-C\equiv C-$, C=O, C=S, $-C(=O)O-$, $-OC(=O)-$, $Si(R^5)_2$, $NR^5$, $-O-$ or $-S-$;

$R^5$ is on each occurrence, identically or differently, H, D, F, Cl, CN, $N(R^6)_2$, an alkyl, alkoxy or thioalkoxy group having 1 to 10 C atoms or an alkenyl or alkynyl group having 2 to 20 C atoms, where the above-mentioned groups may each be substituted by one or more radicals $R^6$ and where one or more $CH_2$ groups in the above-mentioned groups may be replaced by $-R^6C=CR^6-$, $-C\equiv C-$, C=O, C=S, $-C(=O)O-$, $-O(C=O)-$, $Si(R^6)_2$, $NR^6$, $-O-$ or $-S-$, or an aryl or heteroaryl group having 5 to 30 aromatic ring atoms, which may in each case be substituted by one or more radicals $R^6$;

$R^6$ is on each occurrence, identically or differently, H, F or an aliphatic organic radical having 1 to 20 C atoms, in which one or more H atoms may be replaced by F, or an aryl or heteroaryl group having 5 to 20 C atoms, in which one or more H atoms may be replaced by F;

i is equal to 0, 1, 2, 3, 4 or 5.

If i is greater than 1, the groups within the brackets may be identical or different.

If i is equal to 0, the group within the brackets is absent, and the groups $Ar^1$ and $Z^2$ are connected directly to one another.

The formulation "two, three, four or five groups combined with one another, selected from the groups . . . " in the sense of the present application is taken to mean that the groups are bonded to one another, preferably in the form of a chain in which two, three, four or five of the groups are bonded to one another. Preference is given to a combination of precisely two or three groups. The groups can generally be identical or different.

An aryl group in the sense of this invention contains 6 to 30 aromatic ring atoms; a heteroaryl group in the sense of this invention contains 5 to 30 aromatic ring atoms, at least one of which is a heteroatom. The heteroatoms are preferably selected from N, O and S. This represents the basic definition. If other preferences are indicated in the description of the present invention, for example with respect to the number of aromatic ring atoms or the heteroatoms present, these apply.

An aryl group or heteroaryl group here is taken to mean either a simple aromatic ring, i.e. benzene, or a simple heteroaromatic ring, for example pyridine, pyrimidine or thiophene, or a condensed (annellated) aromatic or heteroaromatic polycycle, for example naphthalene, phenanthrene, quinoline or carbazole. A condensed (annellated) aromatic or heteroaromatic polycycle in the sense of the present application consists of two or more simple aromatic or heteroaromatic rings condensed with one another. A polycycle of this type may also contain individual non-conjugated units, as in the case, for example, of the fluorene basic structure.

An aryl or heteroaryl group, which may in each case be substituted by the above-mentioned radicals and which may be linked to the aromatic or heteroaromatic ring system via any desired positions, is taken to mean, in particular, groups derived from benzene, naphthalene, anthracene, phenanthrene, pyrene, dihydropyrene, chrysene, perylene, fluoranthene, benzanthracene, benzophenanthrene, tetracene, pentacene, benzopyrene, fluorene, spirobifluorene, furan, benzofuran, isobenzofuran, dibenzofuran, thiophene, benzothiophene, isobenzothiophene, dibenzothiophene, benzodithiophene, cyclopentadithiophene, thienothiophene, indenothiophene, dithienopyrrole, silolodithiophene, selenophene, benzoselenophene, dibenzoselenophene, pyrrole, indole, isoindole, carbazole, pyridine, quinoline, isoquinoline, acridine, phenanthridine, benzo-5,6-quinoline, benzo-6,7-quinoline, benzo-7,8-quinoline, phenothiazine, phenoxazine, pyrazole, indazole, imidazole, benzimidazole, naphthimidazole, phenanthrimidazole, pyridimidazole, pyrazinimidazole, quinoxalinimidazole, oxazole, benzoxazole, naphthoxazole, anthroxazole, phenanthroxazole, isoxazole, 1,2-thiazole, 1,3-thiazole, benzothiazole, pyridazine, benzopyridazine, pyrimidine, benzopyrimidine, quinoxaline, pyrazine, phenazine, naphthyridine, azacarbazole, benzocarboline, phenanthroline, 1,2,3-triazole, 1,2,4-triazole, benzotriazole, 1,2,3-oxadiazole, 1,2,4-oxadiazole, 1,2,5-oxadiazole, 1,3,4-oxadiazole, 1,2,3-thiadiazole, 1,2,4-thiadiazole, 1,2,5-thiadiazole, 1,3,4-thiadiazole, 1,3,5-triazine, 1,2,4-triazine, 1,2,3-triazine, tetrazole, 1,2,4,5-tetrazine, 1,2,3,4-tetrazine, 1,2,3,5-tetrazine, purine, pteridine, indolizine and benzothiadiazole.

For the purposes of the present invention, an alkyl group having 1 to 10 C atoms or an alkenyl or alkynyl group having 2 to 10 C atoms, in which, in addition, individual H atoms or $CH_2$ groups may be substituted by the groups mentioned above under the definition of the radicals, is preferably taken to mean the radicals methyl, ethyl, n-propyl, i-propyl, n-butyl, i-butyl, s-butyl, t-butyl, 2-methylbutyl, n-pentyl, s-pentyl, cyclopentyl, neopentyl, n-hexyl, cyclohexyl, neohexyl, n-heptyl, cycloheptyl, n-octyl, cyclooctyl, 2-ethylhexyl, trifluoromethyl, pentafluoroethyl, 2,2,2-trifluoroethyl, ethenyl, propenyl, butenyl, pentenyl, cyclopentenyl, hexenyl, cyclohexenyl, heptenyl, cycloheptenyl, octenyl, cyclooctenyl, ethynyl, propynyl, butynyl, pentynyl, hexynyl or octynyl.

An alkoxy or thioalkoxy group having 1 to 10 C atoms is preferably taken to mean methoxy, trifluoromethoxy, ethoxy, n-propoxy, i-propoxy, n-butoxy, i-butoxy, s-butoxy, t-butoxy, n-pentoxy, s-pentoxy, 2-methylbutoxy, n-hexoxy, cyclohexyloxy, n-heptoxy, cycloheptyloxy, n-octyloxy, cyclooctyloxy, 2-ethylhexyloxy, pentafluoroethoxy, 2,2,2-trifluoroethoxy, methylthio, ethylthio, n-propylthio, i-propylthio, n-butylthio, i-butylthio, s-butylthio, t-butylthio, n-pentylthio, s-pentylthio, n-hexylthio, cyclohexylthio, n-heptylthio, cycloheptylthio, n-octylthio, cyclooctylthio, 2-ethylhexylthio, trifluoromethylthio, pentafluoroethylthio, 2,2,2-trifluoroethylthio, ethenylthio, propenylthio, butenylthio, pentenylthio, cyclopentenylthio, hexenylthio, cyclohexenylthio, heptenylthio, cycloheptenylthio, octenylthio, cyclooctenylthio, ethynylthio, propynylthio, butynylthio, pentynylthio, hexynylthio, heptynylthio or octynylthio.

An aliphatic organic radical having 1 to 20 C atoms is in principle taken to mean any desired organic radical which is not aromatic or heteroaromatic. This is preferably taken to mean alkyl groups having 1 to 10 C atoms, alkoxy groups having 1 to 10 C atoms or alkenyl or alkynyl groups having 2 to 10 C atoms, as described in greater detail above.

Preferably, at most one group X in the compound of the formula (I) or formula (II) stands for N. It is generally preferred in accordance with the invention for X to stand for $CR^2$.

It is furthermore preferred for Y to stand for S.

$Z^1$ preferably stands on each occurrence, identically or differently, for a single bond, —$CR^3$=$CR^3$— or —C≡C—, particularly preferably for a single bond.

$Z^2$ preferably stands on each occurrence, identically or differently, for a single bond, —$C(R^3)_2C(R^3)_2$—, —$CR^3$=$CR^3$—, —C≡C—, —$OC(R^3)_2$— or —$C(R^3)_2O$—, particularly preferably for a single bond, —$CH_2CH_2$—, —$CF_2CF_2$—, —CH=CH—, —CF=CF—, —C≡C—, —$OCH_2$—, —$OCF_2$—, —$CH_2O$— or —$CF_2O$—.

$Ar^1$ preferably represents on each occurrence, identically or differently, an aryl group having 6 to 15 C atoms or a heteroaryl group having 5 to 15 C atoms, which may be substituted by one or more radicals $R^4$. $Ar^1$ is particularly preferably selected on each occurrence, identically or differently, from benzene, fluorene, naphthalene, pyridine, pyrimidine, pyrazine, triazine, thiophene, thiophene with condensed-on 1,4-dioxane ring, benzothiophene, dibenzothiophene, benzodithiophene, cyclopentadithiophene, thienothiophene, indenothiophene, dithienopyrrole, silolodithiophene, selenophene, benzoselenophene, dibenzoselenophene, furan, benzofuran, dibenzofuran and quinoline, each of which is optionally substituted by radicals $R^4$.

The group $R^1$ is preferably on each occurrence, identically or differently, H, F, CN, $N(R^5)_2$, or a straight-chain alkyl or alkoxy group having 1 to 10 C atoms, which may be substituted by one or more radicals $R^5$, or a branched alkyl or alkoxy group having 3 to 10 C atoms, which may be substituted by one or more radicals $R^5$, or a cyclic alkyl group having 4 to 8 C atoms, which may be substituted by one or more radicals $R^5$, where one or more $CH_2$ groups in the alkyl and alkoxy groups may be replaced by —O—, —S— or —$R^5C$≡$CR^5$—, or a siloxanyl group having 1 to 10 Si atoms, which may be substituted by one or more radicals $R^5$.

$R^1$ is very particularly preferably on each occurrence, identically or differently, H, F, or a straight-chain alkyl or alkoxy group having 3 to 8 C atoms, which may be substituted by one or more radicals $R^5$, or a branched alkyl or alkoxy group having 3 to 8 C atoms, which may be substituted by one or more radicals $R^5$, or a cyclic alkyl group having 6 C atoms, which may be substituted by one or more radicals $R^5$, where one or more $CH_2$ groups in the alkyl and alkoxy groups may be replaced by —O—, —S— or —$R^5C$=$CR^5$—, or a siloxanyl group having 1 to 6 Si atoms, which may be substituted by one or more radicals $R^5$.

The group $R^2$ is preferably on each occurrence, identically or differently, H, F, Cl, CN, or an alkyl or alkoxy group having 1 to 10 C atoms, which may be substituted by one or more radicals $R^5$. $R^2$ is very particularly preferably on each occurrence, identically or differently, H, F or Cl. $R^2$ is most preferably equal to H.

$R^3$ is preferably on each occurrence, identically or differently, H, F, or an alkyl group having 1 to 10 C atoms, which may be substituted by one or more radicals $R^5$. $R^3$ is particularly preferably on each occurrence, identically or differently, H or F.

$R^4$ is preferably on each occurrence, identically or differently, H, D, F, CN, or an alkyl or alkoxy group having 1 to 10 C atoms, which may be substituted by one or more radicals $R^5$. $R^4$ is particularly preferably on each occurrence, identically or differently, H or F.

$R^5$ is on each occurrence, identically or differently, H, F, CN, or an alkyl or alkoxy group having 1 to 10 C atoms, which may be substituted by one or more radicals $R^6$, or an aryl or heteroaryl group having 5 to 30 aromatic ring atoms, which may in each case be substituted by one or more radicals $R^6$, or a siloxanyl group having 1 to 6 Si atoms, which may be substituted by one or more radicals $R^6$.

The index i is preferably equal to 1, 2 or 3, particularly preferably equal to 1 or 2, very particularly preferably equal to 1.

Preferred embodiments of the formula (I) are the following formulae (I-1) and (I-2)

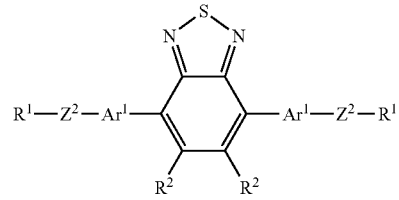

formula (I-1)

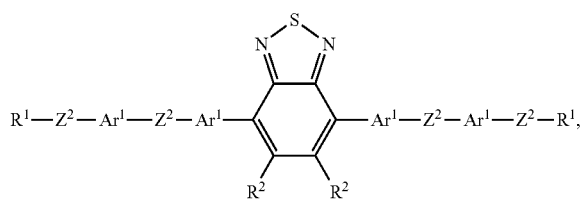

formula (I-2)

where the groups occurring are as defined above.

For formulae (I-1) and (I-2), the above-mentioned preferred embodiments of the groups $Ar^1$, $Z^2$, $R^1$ and $R^2$ preferably apply.

For formulae (I-1) and (I-2), it is preferred for at least one $Ar^1$ bonded directly to benzothiadiazole to stand for a sulfur-containing heteroaryl group, particularly preferably for thiophene. The group may be substituted by one or more radicals $R^4$. Compounds of this type are distinguished by particularly high light stability.

For formulae (I-1) and (I-2), it is particularly preferred for $R^2$ to stand for H, F or Cl, particularly preferably for H.

Preferred embodiments of compounds of the formulae (I-1) and (I-2) conform to the formulae (I-1-1) to (I-1-4) and (I-2-1) to (I-2-4)

formula (I-1-1)
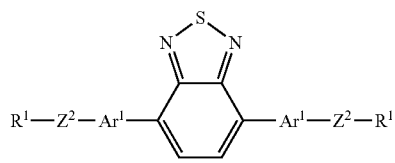

formula (I-1-2)
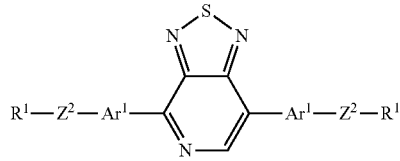

formula (I-1-3)
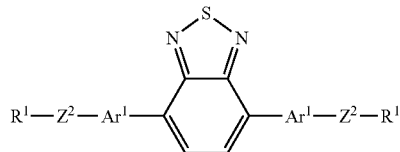

formula (I-1-4)
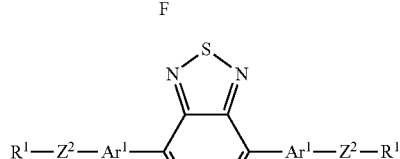

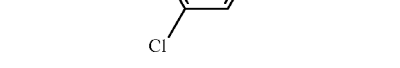

formula (I-2-1)
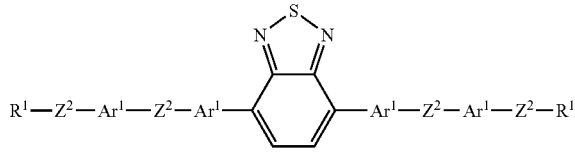

formula (I-2-2)
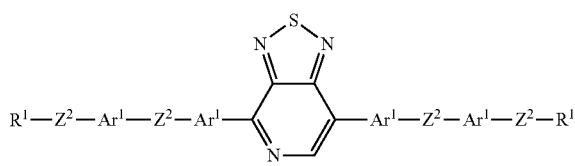

formula (I-2-3)
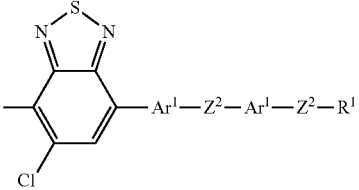

formula (I-2-4)
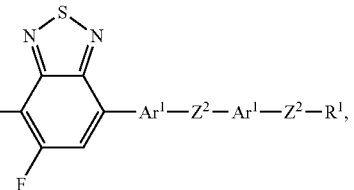
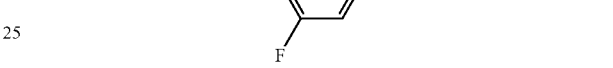

where the groups $Ar^1$, $Z^2$ and $R^1$ occurring are as defined above.

For formulae (I-1-1) to (I-1-4) and (I-2-1) to (I-2-4), the above-mentioned preferred embodiments of the groups $Ar^1$, $Z^2$ and $R^1$ preferably apply.

Of the formulae (I-1-1) to (I-1-4) and (I-2-1) to (I-2-4), the formulae (I-1-1) and (I-2-1) are particularly preferred.

Preferred embodiments of compounds of the formulae (I-1-1) and (I-2-1) are the following formulae (I-1-1-1) to (I-1-1-4) and (I-2-1-1) to (I-2-1-4):

formula (I-1-1-1)
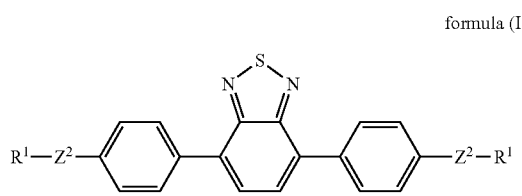

formula (I-1-1-2)
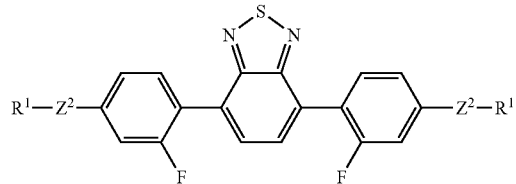

formula (I-1-1-3)
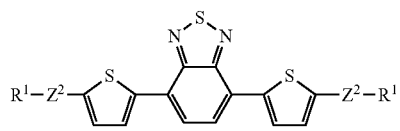

formula (I-1-1-4)
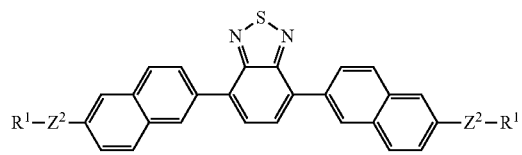

formula (I-2-1-1)

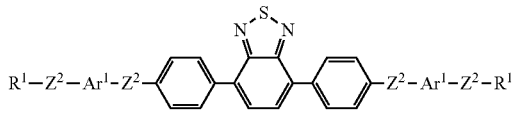

formula (I-2-1-2)

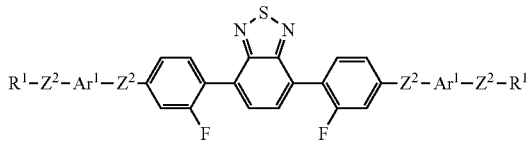

formula (I-2-1-3)

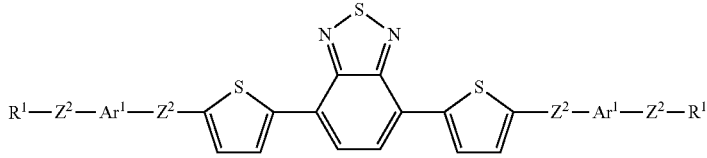

formula (I-2-1-4)

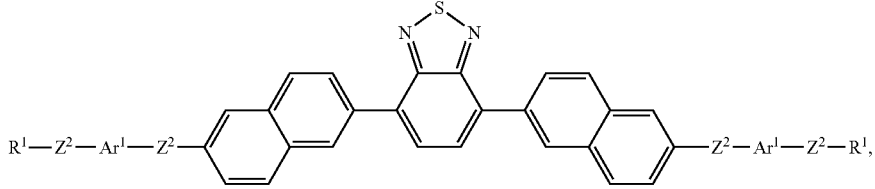

where the groups Ar$^1$, Z$^2$ and R$^1$ occurring are defined as above.

For formulae (I-1-1-1) to (I-1-1-4) and (I-2-1-1) to (I-2-1-4), the above-mentioned preferred embodiments of the groups Ar$^1$, Z$^2$ and R$^1$ preferably apply.

Concerning the above-described preferred embodiments of the variable groups of formula (I) or formula (II), it is preferred for them to occur in combination with one another.

The present invention furthermore relates to specific compounds of the formula (I) which conform to the following formulae (Ia) and (Ib)

n is, identically or differently on each occurrence, 1, 2, 3, 4 or 5.

In a preferred embodiment, the index k in the above-mentioned formulae is, identically or differently, 0 or 1, particularly preferably identically 0.

In a preferred embodiment, the index m in the above-mentioned formulae is, identically or differently, 0, 1 or 2, particularly preferably identically 1 or 2.

In a preferred embodiment, the index n in the above-mentioned formulae is, identically or differently, 1, 2 or 3, particularly preferably identically 2.

formula (Ia)

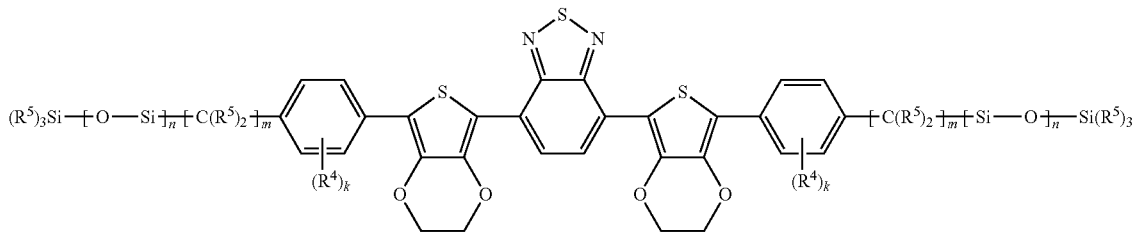

formula (Ib)

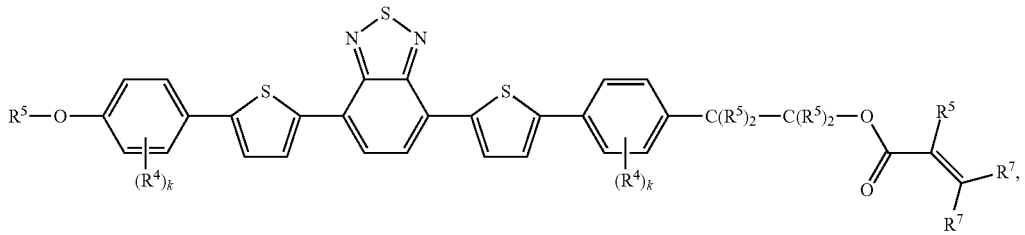

where:
the groups R$^4$ and R$^5$ occurring are defined as above, R$^7$ is defined like R$^5$ above, and
k is, identically or differently on each occurrence, 0, 1, 2, 3 or 4;
m is, identically or differently on each occurrence, 0, 1, 2, 3, 4, 5 or 6;

Furthermore preferably, R$^5$ in the above-mentioned formulae is hydrogen or an alkyl group having 1 to 5 C atoms, which may be substituted by one or more radicals R$^6$, particularly preferably methyl.

In a preferred embodiment, R$^7$ in the above-mentioned formulae is hydrogen or an alkyl group having 1 to 5 C atoms, which may be substituted by one or more radicals R⁶, particularly preferably hydrogen.

The compounds of the formulae (Ia) and (Ib) have particularly great advantages in relation to the above-mentioned properties of good solubility in the liquid-crystalline medium, good light stability, high fluorescence and/or high anisotropy of the absorption or dichroic behaviour.

The present invention furthermore relates to specific compounds of the formula (II) which conform to the following formula (IIa)

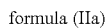
formula (IIa)

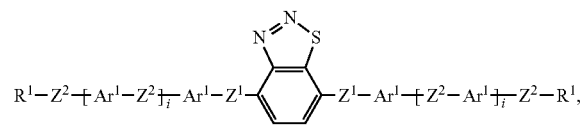

where:
the groups $R^1$, $Ar^1$, $Z^1$ and $Z^2$ occurring and the index i are defined as above.

In a preferred embodiment, the index i in the above-mentioned formula (IIa) is, identically or differently, 0, 1 or 2, particularly preferably identically 1.

Furthermore preferably, $Z^1$ in the above-mentioned formula (IIa) is a single bond.

In a preferred embodiment, $Ar^1$ in the above-mentioned formula (IIa) is an $R^4$-substituted aryl radical, particularly preferably $R^4$-substituted benzene, fluorene, naphthalene, pyridine, pyrimidine, pyrazine, triazine, thiophene, thiophene with condensed-on 1,4-dioxane ring, benzothiophene, dibenzothiophene, benzodithiophene, cyclopentadithiophene, thienothiophene, indenothiophene, dithienopyrrole, silolodithiophene, selenophene, benzoselenophene, dibenzoselenophene, furan, benzofuran, dibenzofuran or quinoline.

The following compounds are examples of compounds of the formula (I) or formula (II):

TABLE 1

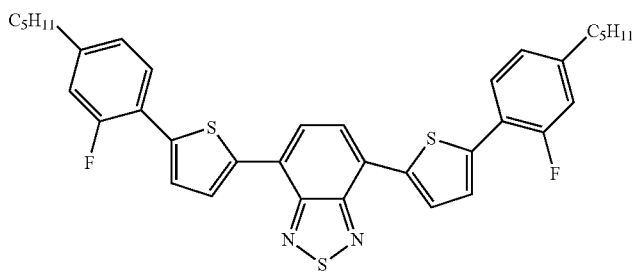

(1)

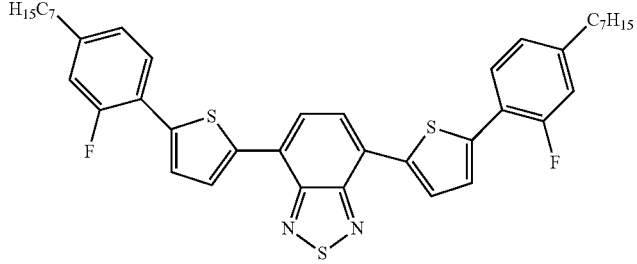

(2)

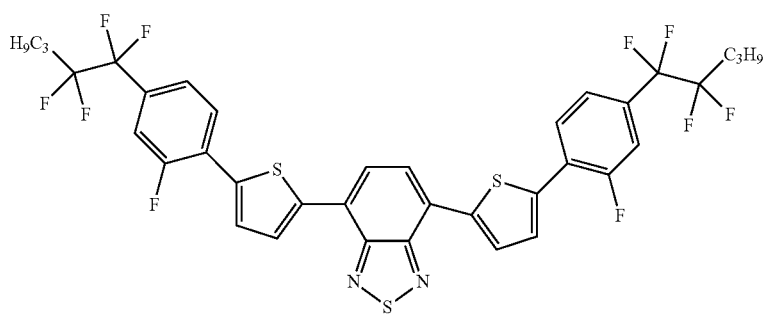

(3)

TABLE 1-continued
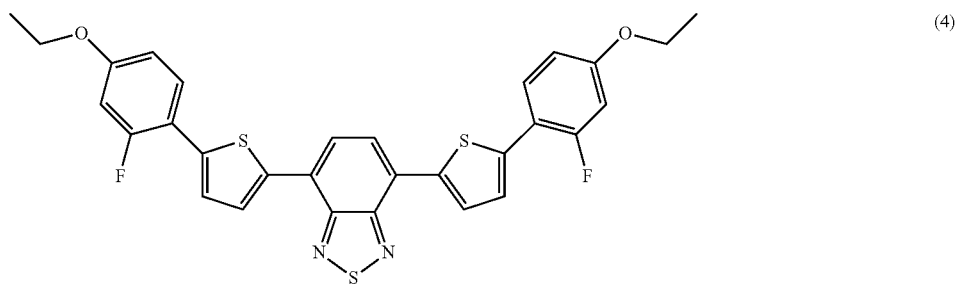
(4)
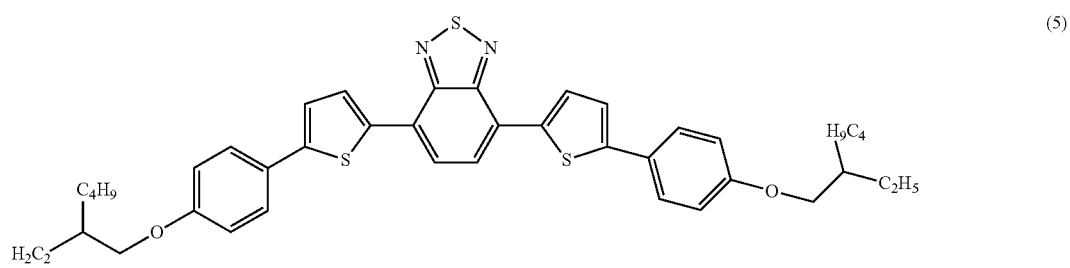
(5)
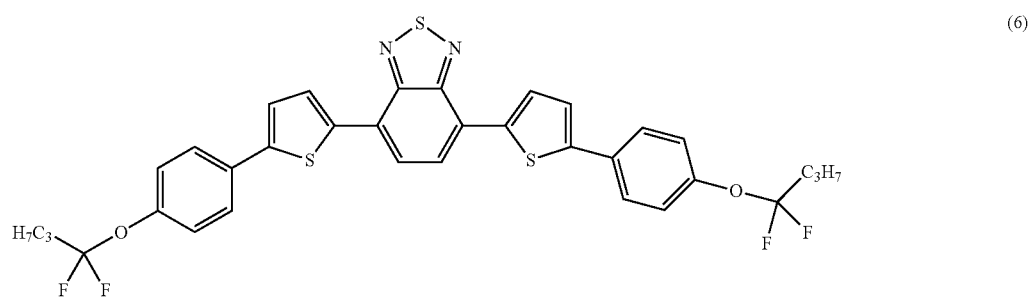
(6)
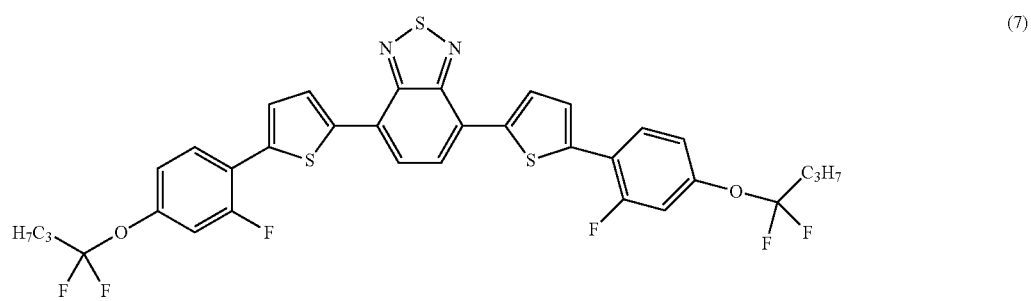
(7)
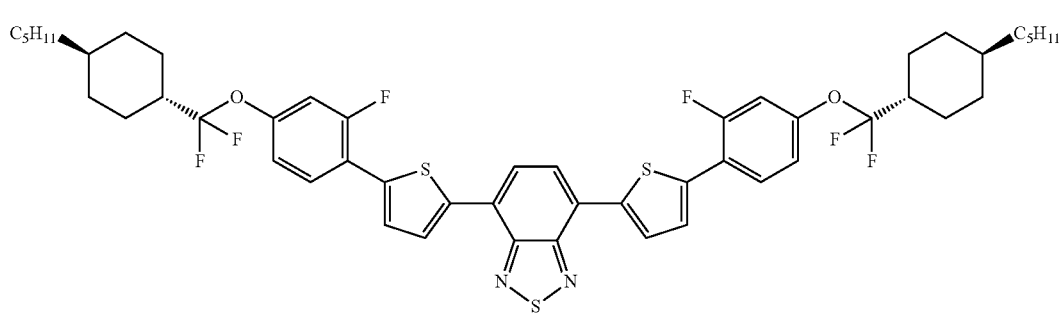
(8)

TABLE 1-continued
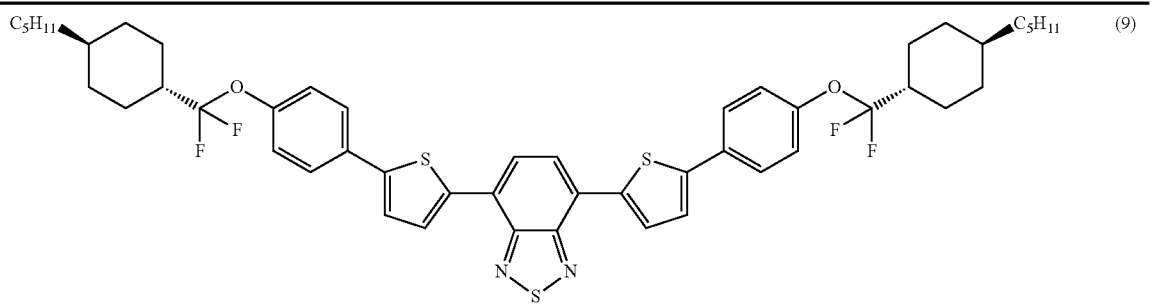
(9)
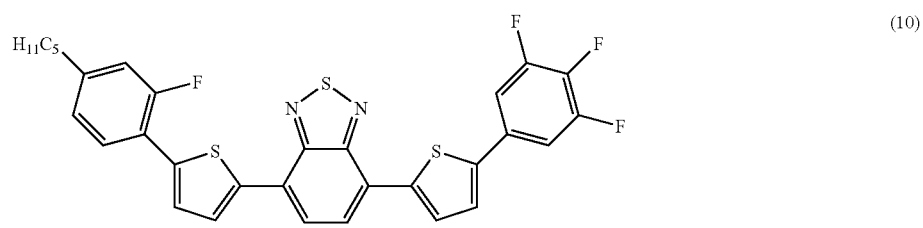
(10)
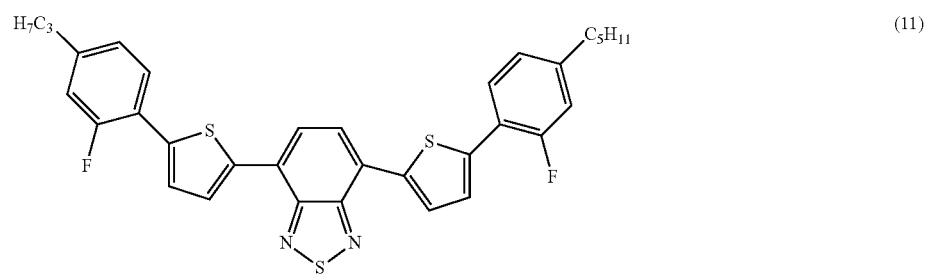
(11)
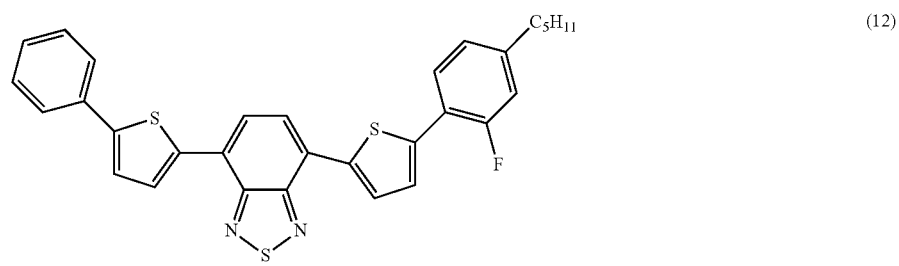
(12)
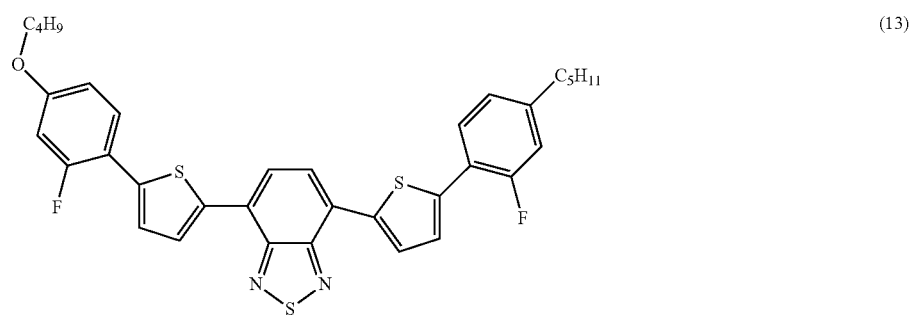
(13)
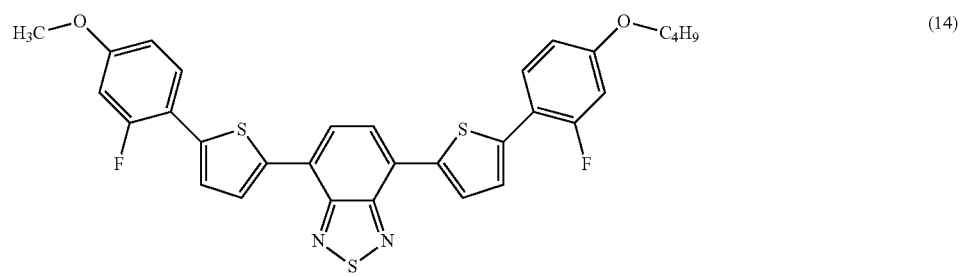
(14)

TABLE 1-continued
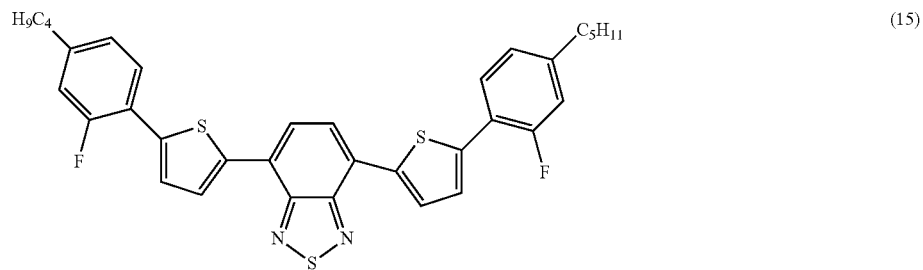 (15)
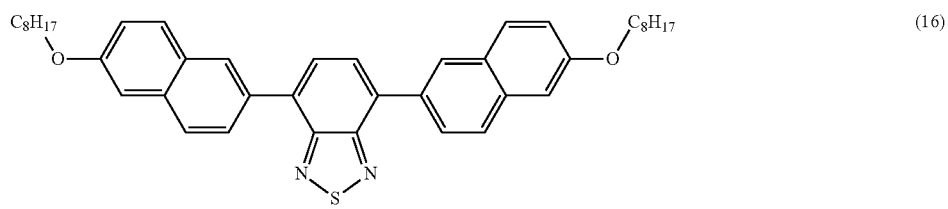 (16)
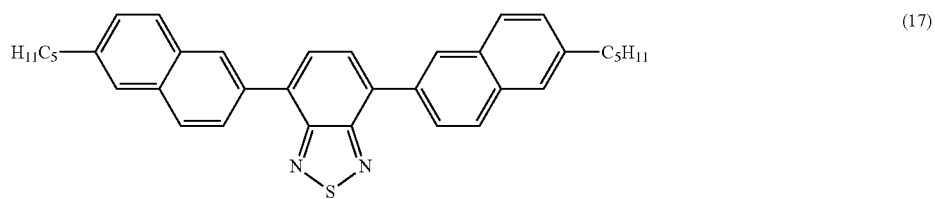 (17)
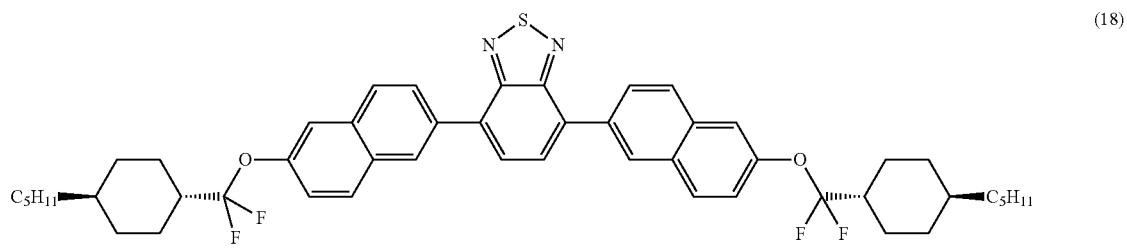 (18)
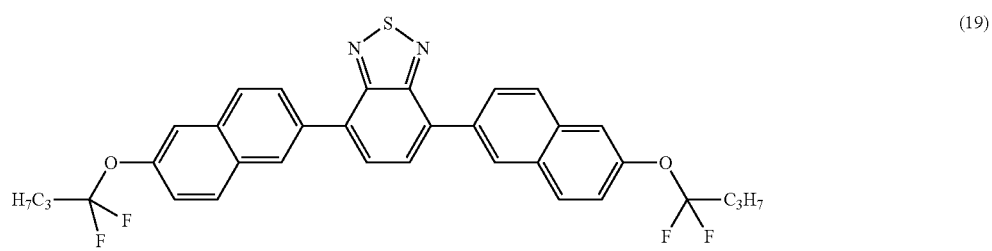 (19)
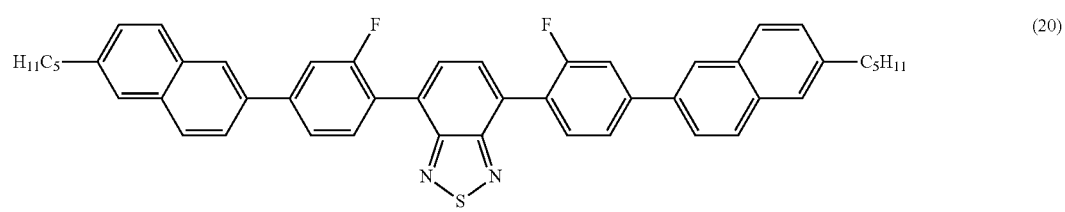 (20)
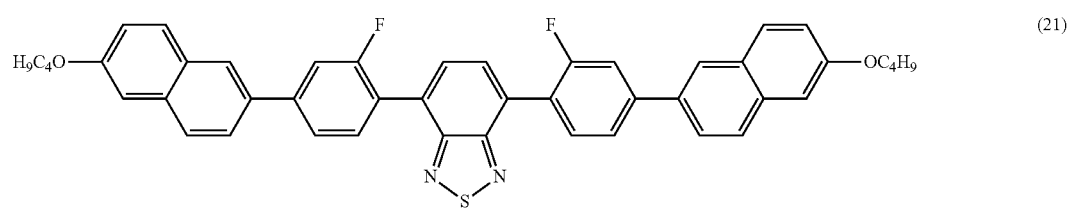 (21)

TABLE 1-continued
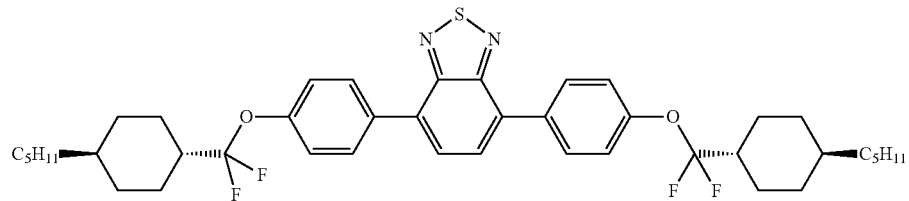
(22)
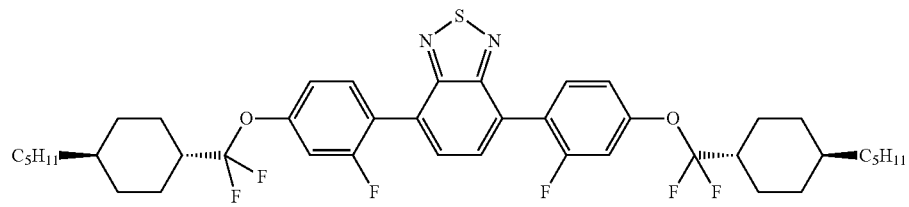
(23)
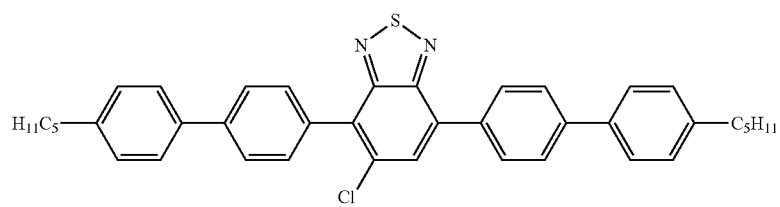
(24)
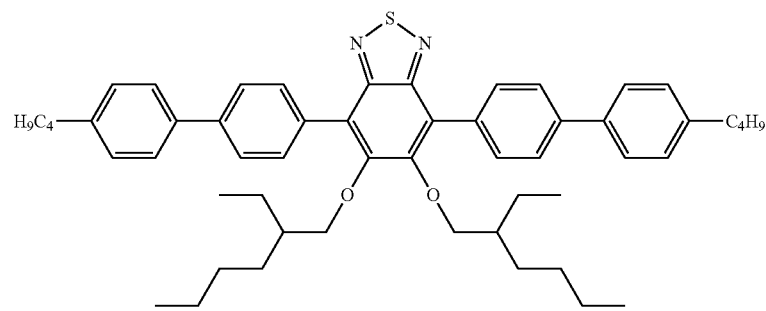
(25)
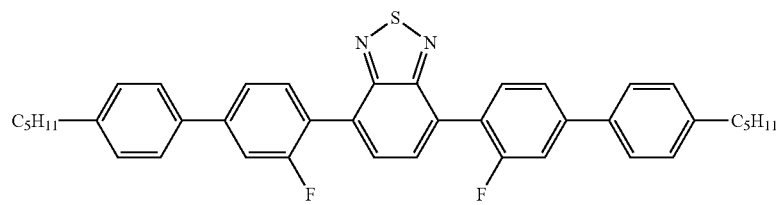
(26)
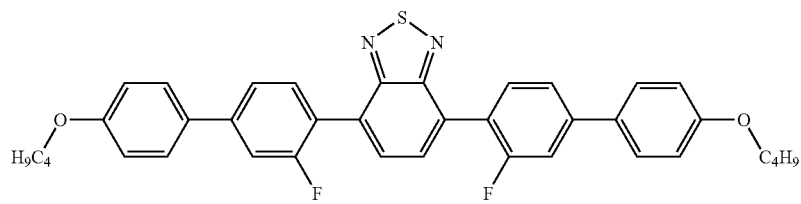
(27)
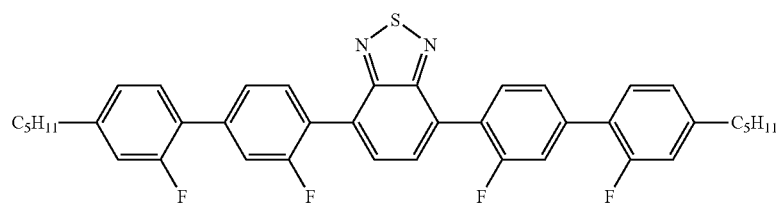
(28)

TABLE 1-continued
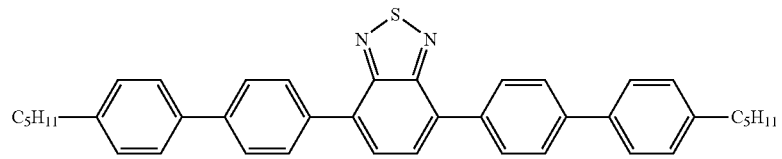 (29)
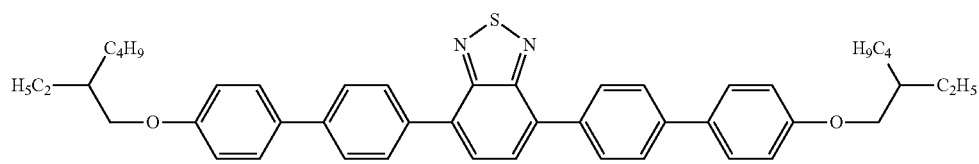 (30)
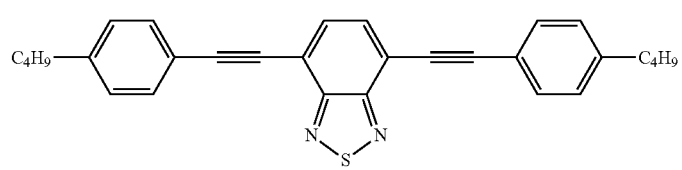 (31)
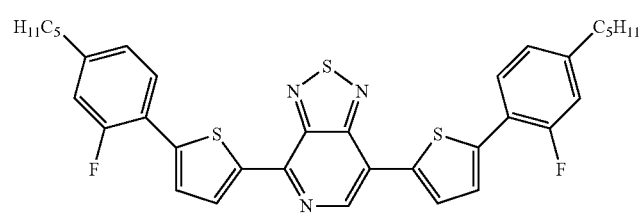 (32)
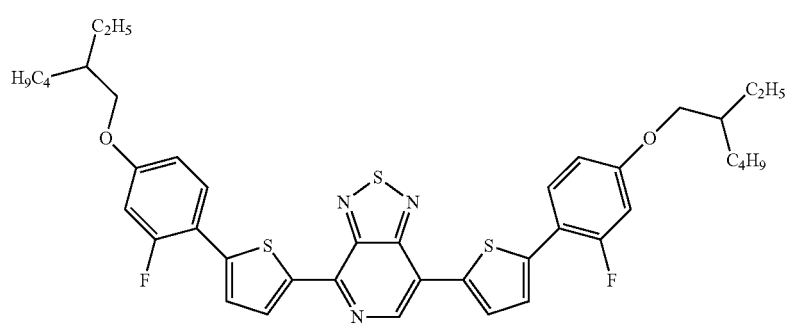 (33)
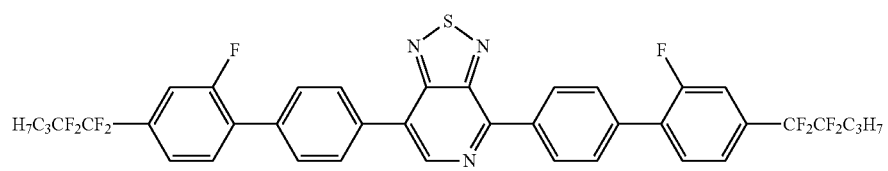 (34)
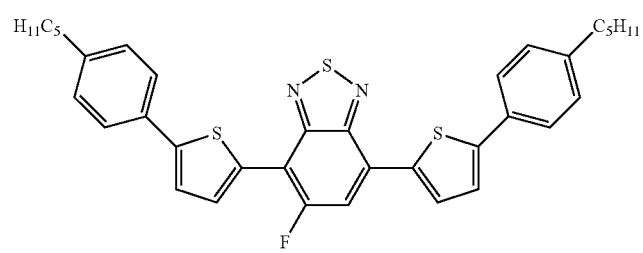 (35)

TABLE 1-continued
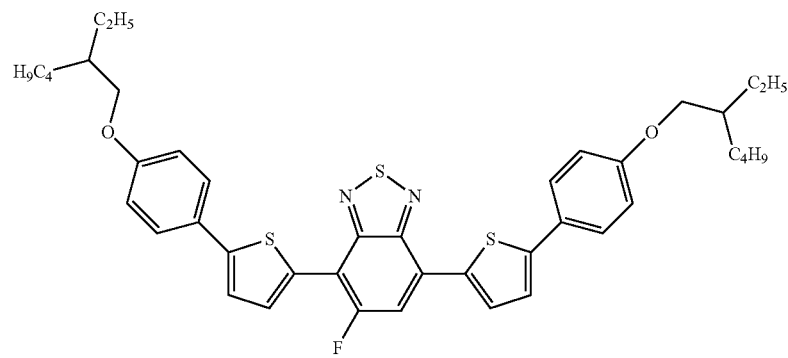
(36)
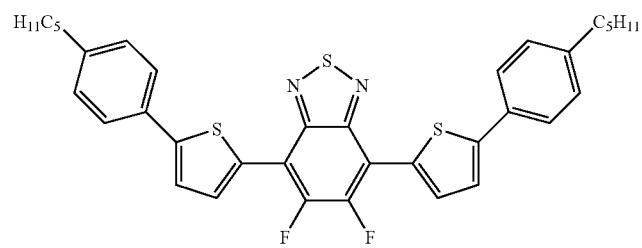
(37)
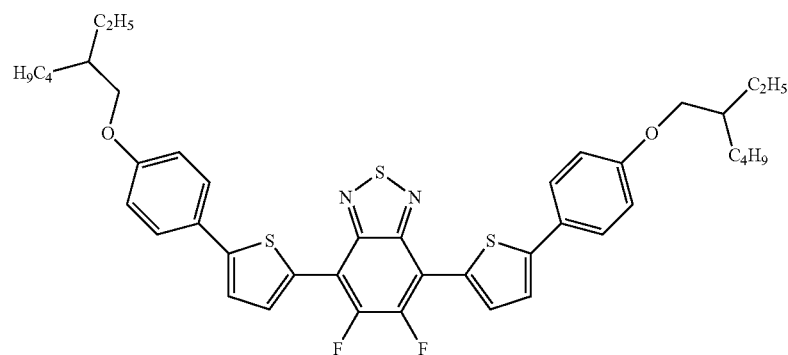
(38)
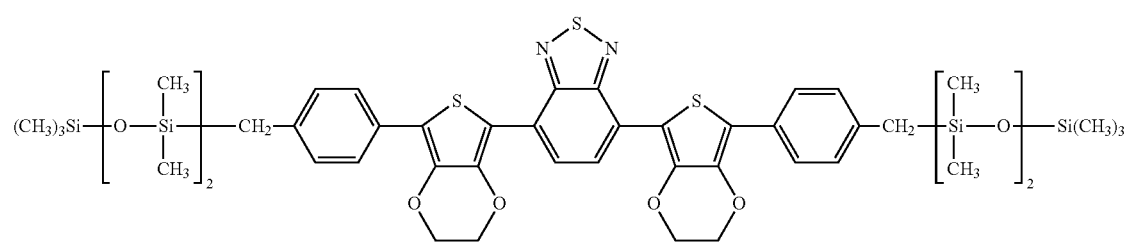
(39)
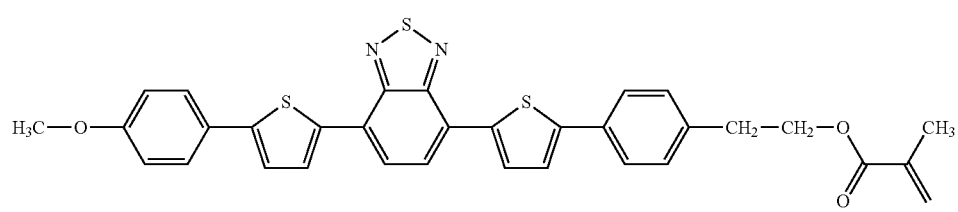 [SMILES: C=C(C)C(=O)OCCc1ccc(-c2ccc(-c3ccc(-c4ccc(-c5ccc(OC)cc5)s4)c4nsnc34)s2)cc1]
(40)
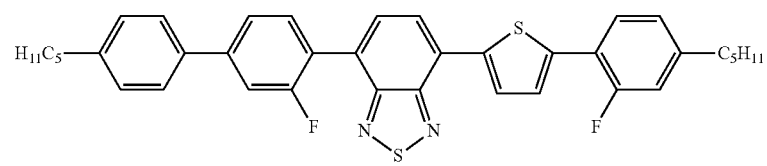
(41)

TABLE 1-continued
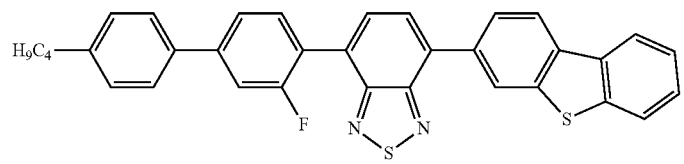
(42)
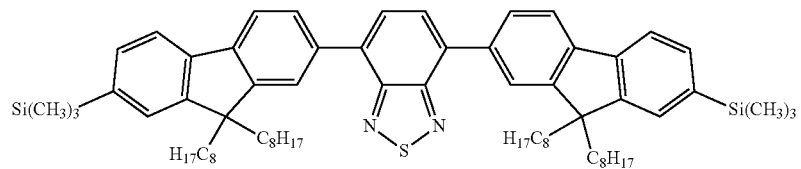
(43)
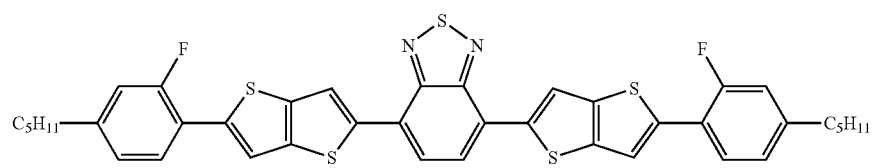
(44)
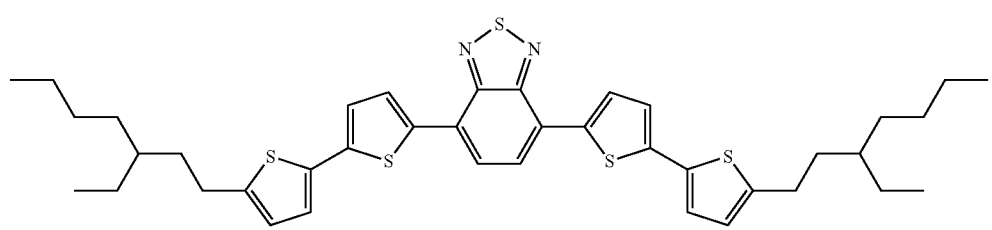 [SMILES: CCCCC(CC)CCc1ccc(-c2ccc(-c3ccc(-c4ccc(-c5ccc(CCC(CC)CCCC)s5)s4)c4nsnc34)s2)s1]
(45)
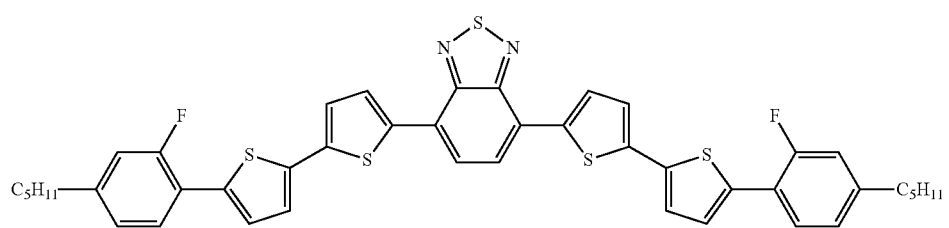
(46)
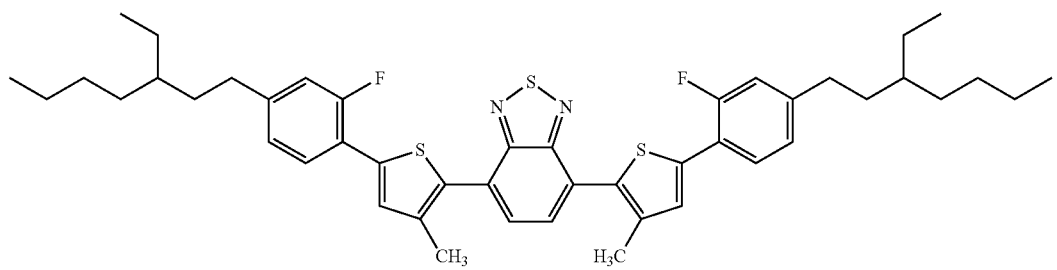 [SMILES: CCCCC(CC)CCc1ccc(-c2cc(C)c(-c3ccc(-c4sc(-c5ccc(CCC(CC)CCCC)cc5F)cc4C)c4nsnc34)s2)c(F)c1]
(47)
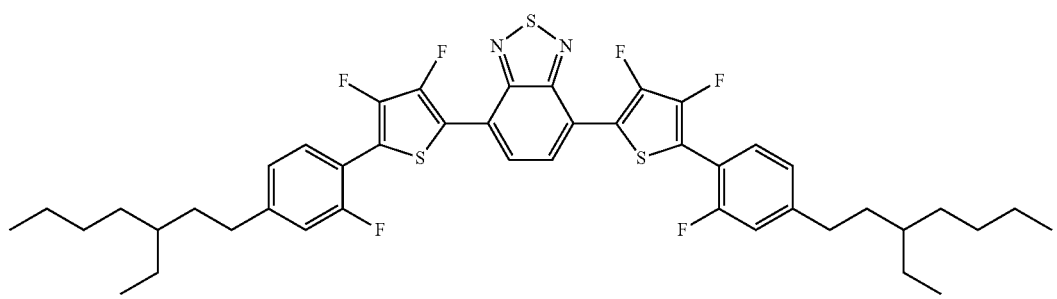 [SMILES: CCCCC(CC)CCc1ccc(-c2sc(-c3ccc(-c4sc(-c5ccc(CCC(CC)CCCC)cc5F)c(F)c4F)c4nsnc34)c(F)c2F)c(F)c1]
(48)

TABLE 1-continued

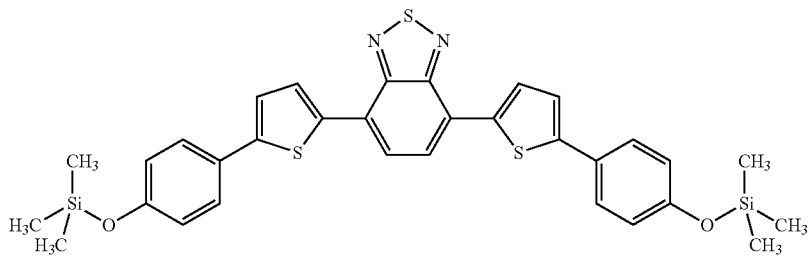
(49)

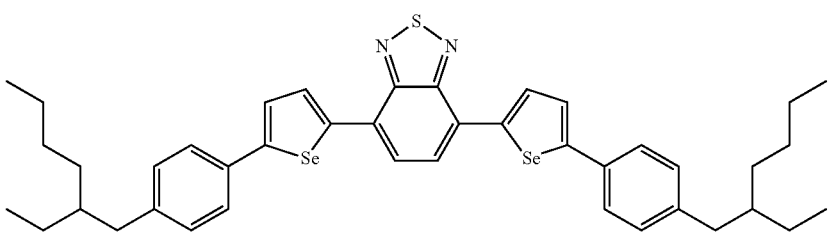 [SMILES: CCCCC(CC)Cc1ccc(-c2ccc(-c3ccc(-c4ccc(-c5ccc(CC(CC)CCCC)cc5)[se]4)c4nsnc34)[se]2)cc1]
(50)

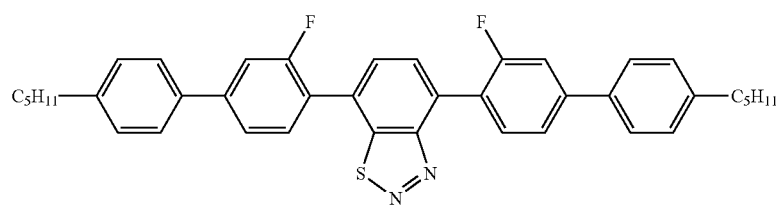
(51)

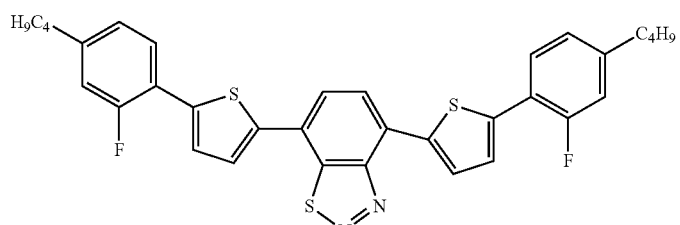
(52)

The compounds of the formula (I) and formula (II) can be prepared by known processes of organic chemistry, in particular by Suzuki coupling between organic bromides and organic boronic acids. Particularly suitable processes are shown below in general form. For specific processes for the preparation of compounds of the formula (I) and formula (II), reference is furthermore made to the known literature and to the working examples.

A possible, preferred process for the preparation of compounds of the formula (I) and formula (II) is based on a benzothiadiazole derivative which carries two bromine or chlorine substituents. Compounds of the formula (I) and formula (II) can be prepared therefrom by Suzuki coupling to suitable boronic acid derivatives, as shown by Schemes 1 and 2 below.

Scheme 1

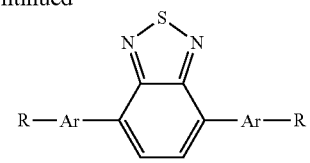

-continued

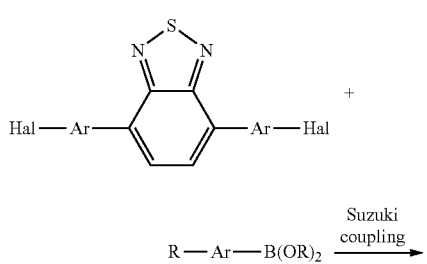

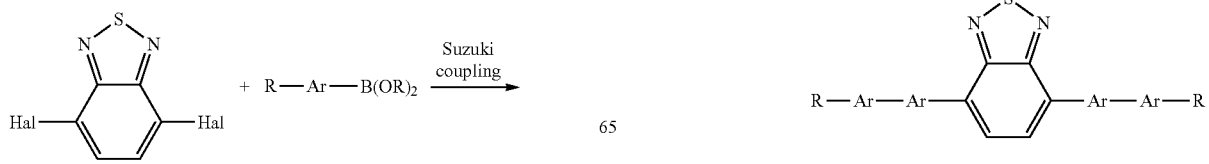

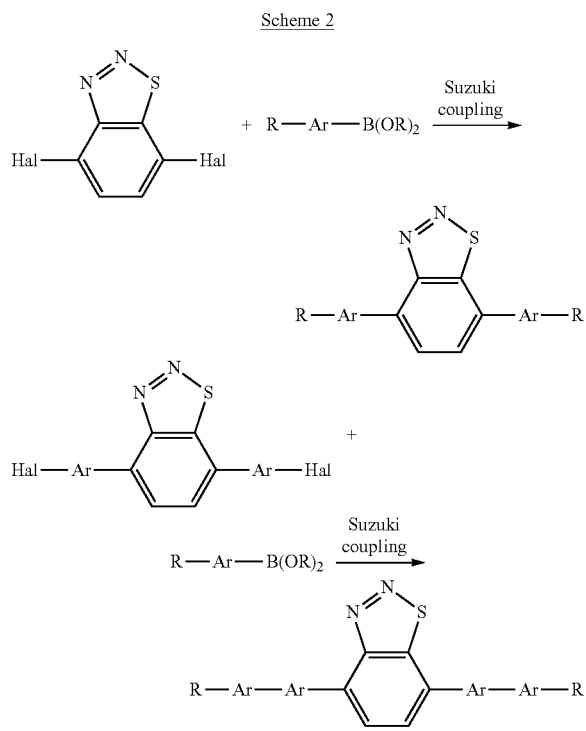

Scheme 2

The compound of the formula (I) or formula (II) is preferably a positively dichroic dye, i.e. a dye which has a positive degree of anisotropy R, determined as indicated in the working examples. The degree of anisotropy R is particularly preferably greater than 0.4, very particularly preferably greater than 0.6 and most preferably greater than 0.7, where R is determined as indicated in the working examples.

The absorption preferably reaches a maximum when the polarisation direction of the light is parallel to the direction of the longest elongation of the molecule of the formula (I) or formula (II), and it reaches a minimum when the polarisation direction of the light is perpendicular to the direction of the longest elongation of the molecule of the formula (I) or formula (II).

The compound of the formula (I) or formula (II) is furthermore preferably a fluorescent dye. Fluorescence here is taken to mean that a compound is placed in an electronically excited state by absorption of light of a certain wavelength, where the compound subsequently undergoes a transition into the ground state with emission of light. The emitted light preferably has a longer wavelength than the absorbed light. The transition from the excited state into the ground state is furthermore preferably spin-allowed, i.e. takes place without a change in the spin. Furthermore preferably, the lifetime of the excited state of the fluorescent compound is shorter than $10^{-6}$ s, particularly preferably shorter than $10^{-6}$s, very particularly preferably between $10^{-9}$ and $10^{-7}$ s.

The dichroic compound of the formula (I) or formula (II) is preferably present in the switching layer in a proportion of 0.01 to 10% by weight, particularly preferably 0.05 to 7% by weight and very particularly preferably 0.1 to 7% by weight.

Besides the compound of the formula (I) or formula (II), a liquid-crystalline medium comprising one or more different compounds is preferably present in the switching layer. The liquid-crystalline medium preferably represents the principal component of the mixture of the switching layer of the device according to the invention. The dichroic compound of the formula (I) or formula (II) is preferably in the form of a solution in the switching layer. It is preferably influenced in its alignment by the alignment of the compounds of the liquid-crystalline medium.

For the purposes of the present application, the term liquid-crystalline medium is taken to mean a material which has liquid-crystalline properties under certain conditions. The material preferably has liquid-crystalline properties at room temperature and in a certain temperature range above and below room temperature. The liquid-crystalline medium may comprise a single compound, or it may comprise a plurality of different compounds. The liquid-crystalline medium in accordance with the invention typically comprises at least one compound whose molecules have an elongated shape, i.e. are significantly longer in one spatial direction (longitudinal axis) than in the other two spatial directions.

The invention furthermore relates to the use of a mixture comprising a liquid-crystalline medium and at least one compound of a formula (I) or formula (II) in a device for regulating the passage of energy from an outside space into an inside space.

The liquid-crystalline medium of the switching layer preferably has a clearing point, preferably a phase transition from a nematic liquid-crystalline state to an isotropic state, in the temperature range from 70° C. to 170° C., preferably from 90° C. to 160° C., particularly preferably from 95° C. to 150° C. and very particularly preferably from 105° C. to 140° C.

Furthermore, the dielectric anisotropy of the liquid-crystalline medium of the switching layer is preferably greater than 3, particularly preferably greater than 7.

In a further preferred embodiment, the dielectric anisotropy of the liquid-crystalline medium of the switching layer is less than zero, preferably less than −2.

The liquid-crystalline medium of the switching layer furthermore preferably has an optical anisotropy (Δn) of 0.01 to 0.3, particularly preferably of 0.04 to 0.27.

The liquid-crystalline medium of the switching layer furthermore preferably comprises 3 to 20 different liquid-crystalline compounds, preferably 8 to 18, particularly preferably 12 to 16 different liquid-crystalline compounds.

Compounds which can be used as constituents of the liquid-crystalline medium are known to the person skilled in the art and can be selected freely.

It is preferred for the liquid-crystalline medium of the switching layer to comprise at least one compound which contains structural elements based on 1,4-phenylenes and 1,4-cyclohexylenes which are substituted by one or more fluorine atoms or one or more nitrile groups. It is particularly preferred for the liquid-crystalline medium of the switching layer to comprise at least one compound which contains 2, 3 or 4, particularly preferably 3 or 4 structural elements based on 1,4-phenylenes and 1,4-cyclohexylenes.

It is furthermore preferred for the liquid-crystalline medium of the switching layer to comprise one or more chiral dopants. In this case, the molecules of the liquid-crystalline medium are preferably twisted with respect to one another in the switching layer of the device, particularly preferably as known from the TN mode of displays.

Chiral dopants are preferably used in the liquid-crystalline medium of the switching layer in a total concentration of 0.01 to 3% by weight, particularly preferably 0.05 to 1% by weight. In order to obtain high values for the twist, the total concentration of the chiral dopants may also be selected higher than 3% by weight, preferably up to a maximum of 10% by weight.

According to an alternative, likewise preferred embodiment, the liquid-crystalline medium of the switching layer comprises no chiral dopants. In this case, the molecules of the liquid-crystalline medium are preferably not twisted with respect to one another in the switching layer of the device.

The proportions of these compounds and other components present in small amounts are neglected when specifying the proportions of the liquid-crystalline compounds and the dichroic dyes.

The liquid-crystalline medium of the switching layer furthermore preferably comprises one or more stabilisers. The total concentration of the stabilisers is preferably between 0.00001 and 10% by weight, particularly preferably between 0.0001 and 1% by weight of the entire mixture. The proportions of these compounds and other components present in small amounts are neglected when specifying the proportions of the liquid-crystalline compounds and the dichroic dyes.

In addition to one or more compounds of the formula (I) or formula (II), and preferably a liquid-crystalline medium, the device according to the invention preferably also comprises further dichroic dyes having a different structure to formula (I) or formula (II) in the switching layer. It particularly preferably comprises one, two, three or four further dyes, very particularly preferably two or three further dyes and most preferably three further dyes having a different structure to formula (I) or formula (II).

With respect to the property of dichroism, the preferred properties described for the compound of the formula (I) or formula (II) are also preferred for the optional further dichroic dyes.

The absorption spectra of the dichroic dyes of the switching layer preferably complement one another in such a way that the impression of a black colour arises for the eye. The two or more dichroic dyes of the liquid-crystalline medium according to the invention preferably cover a large part of the visible spectrum. The precise way in which a mixture of dyes which appears black or grey to the eye can be prepared is known to the person skilled in the art and is described, for example, in Manfred Richter, Einführung in die Farbmetrik [Introduction to Colorimetry], 2nd Edition, 1981, ISBN 3-11-008209-8, Verlag Walter de Gruyter & Co.

The setting of the colour location of a mixture of dyes is described in the area of colorimetry. To this end, the spectra of the individual dyes are calculated taking into account the Lambert-Beer law to give an overall spectrum and converted into the corresponding colour locations and luminance values under the associated illumination, for example illuminant D65 for daylight, in accordance with the rules of colorimetry. The position of the white point is fixed by the respective illuminant, for example D65, and is quoted in tables (for example reference above). Different colour locations can be set by changing the proportions of the various dyes.

According to a preferred embodiment, the switching layer comprises one or more dichroic dyes which absorb light in the red and NIR region, i.e. at a wavelength of 600 to 2000 nm, preferably in the range from 650 to 1800 nm, particularly preferably in the range from 650 to 1300 nm. In a preferred embodiment, these dichroic dyes are selected from azo compounds, anthraquinones, methine compounds, azomethine compounds, merocyanine compounds, naphthoquinones, tetrazines, perylenes, terrylenes, quaterrylenes, higher rylenes, pyrromethenes, azo dyes, nickel dithiolenes, (metal) phthalocyanines, (metal) naphthalocyanines and (metal) porphyrins. Of these, particular preference is given to perylenes and terrylenes. The proportion of all dichroic dyes in the mixture of the switching layer is preferably in total 0.01 to 10% by weight, particularly preferably 0.1 to 7% by weight and very particularly preferably 0.2 to 7% by weight.

The further dichroic dyes of the switching layer having a different structure to formula (I) or formula (II) are furthermore preferably selected from the dye classes indicated in B. Bahadur, Liquid Crystals—Applications and Uses, Vol. 3, 1992, World Scientific Publishing, Section 11.2.1, and particularly preferably from the explicit compounds given in the table present therein.

The said dyes belong to the classes of dichroic dyes which are known to the person skilled in the art and have been described many times in the literature. Thus, for example, anthraquinone dyes are described in EP 34832, EP 44893, EP 48583, EP 54217, EP 56492, EP 59036, GB 2065158, GB 2065695, GB 2081736, GB 2082196, GB 2094822, GB 2094825, JP-A 55-123673, DE 3017877, DE 3040102, DE 3115147, DE 3115762, DE 3150803 and DE 3201120, naphthoquinone dyes are described in DE 3126108 and DE 3202761, azo dyes in EP 43904, DE 3123519, WO 82/2054, GB 2079770, JP-A 56-57850, JP-A 56-104984, U.S. Pat. Nos. 4,308,161, 4,308,162, 4,340,973, T. Uchida, C. Shishido, H. Seki and M. Wada: Mol. Cryst. Liq. Cryst. 39, 39-52 (1977), and H. Seki, C. Shishido, S. Yasui and T. Uchida: Jpn. J. Appl. Phys. 21, 191-192 (1982), and perylenes are described in EP 60895, EP 68427 and WO 82/1191. Rylene dyes as described, for example, in EP 2166040, US 2011/0042651, EP 68427, EP 47027, EP 60895, DE 3110960 and EP 698649.

According to a preferred embodiment, the switching layer of the device according to the invention comprises, besides compounds of the formula (I) or formula (II), exclusively dichroic dyes selected from rylene dyes.

Examples of preferred further dichroic dyes which may be present in the switching layer of the device according to the invention are depicted in the following table:

TABLE 2

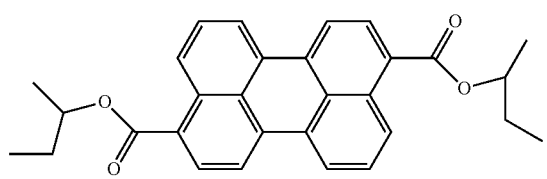 [SMILES: CCC(C)OC(=O)c1ccc2c3cccc4c(C(=O)OC(C)CC)ccc(c5cccc1c52)c43]

TABLE 2-continued
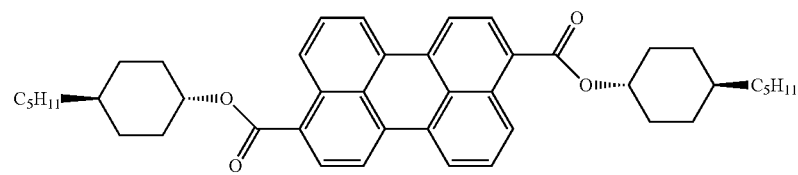
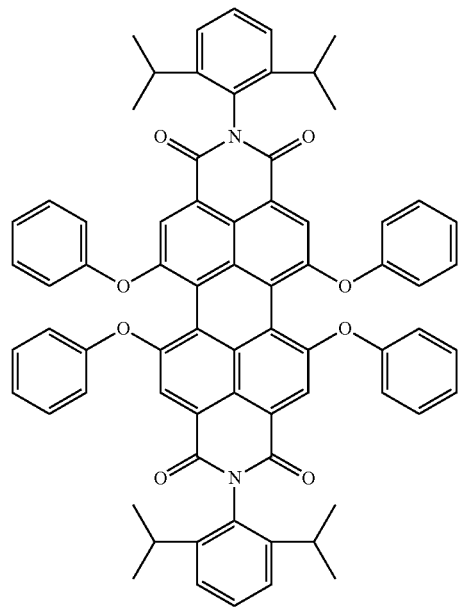 [SMILES: CC(C)c1cccc(C(C)C)c1N1C(=O)c2cc(Oc3ccccc3)c3c4c(Oc5ccccc5)cc5c6c(cc(Oc7ccccc7)c(c7c(Oc8ccccc8)cc(c2c37)C1=O)c64)C(=O)N(c1c(C(C)C)cccc1C(C)C)C5=O]
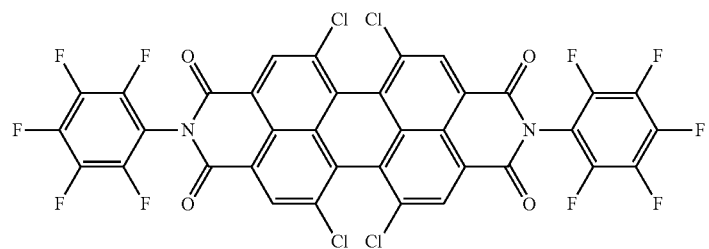 [SMILES: O=C1c2cc(Cl)c3c4c(Cl)cc5c6c(cc(Cl)c(c7c(Cl)cc(c2c37)C(=O)N1c1c(F)c(F)c(F)c(F)c1F)c64)C(=O)N(c1c(F)c(F)c(F)c(F)c1F)C5=O]
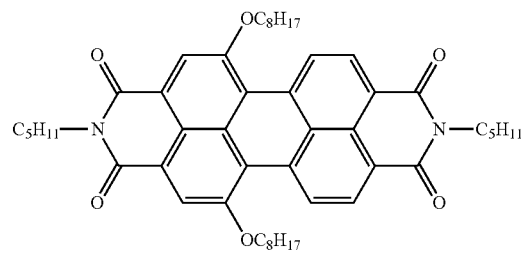
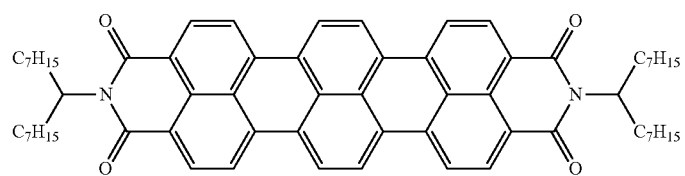

TABLE 2-continued
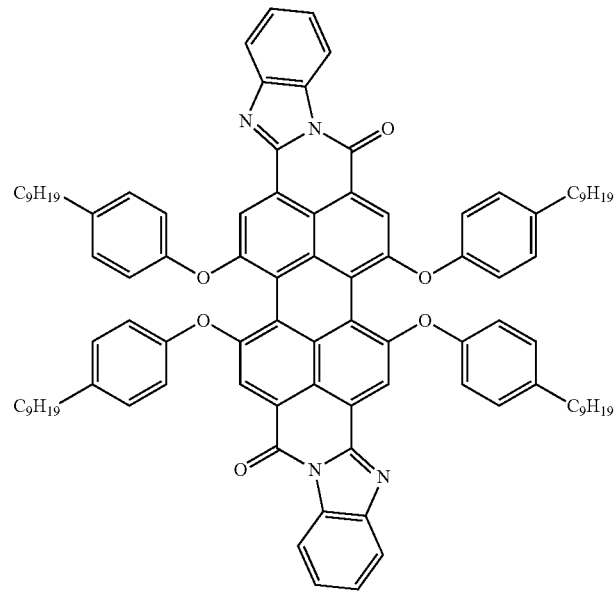
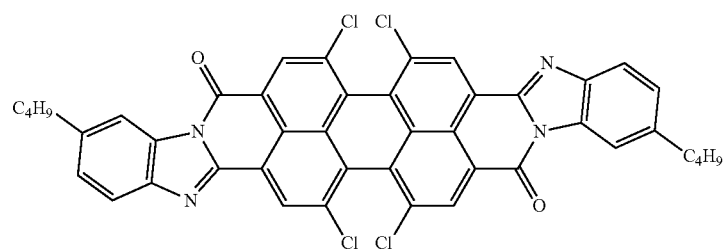
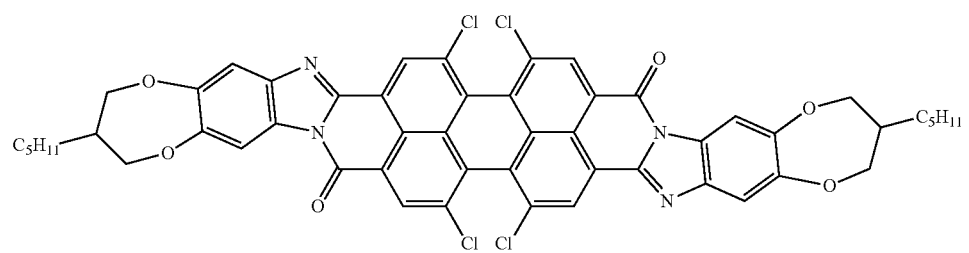
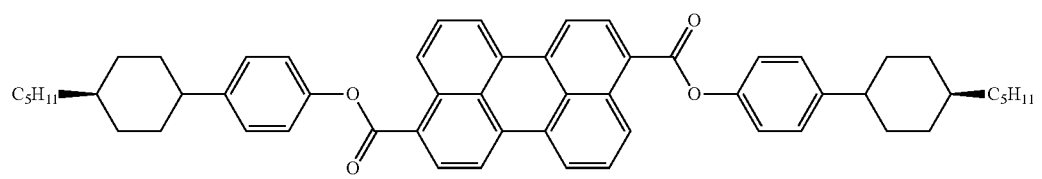
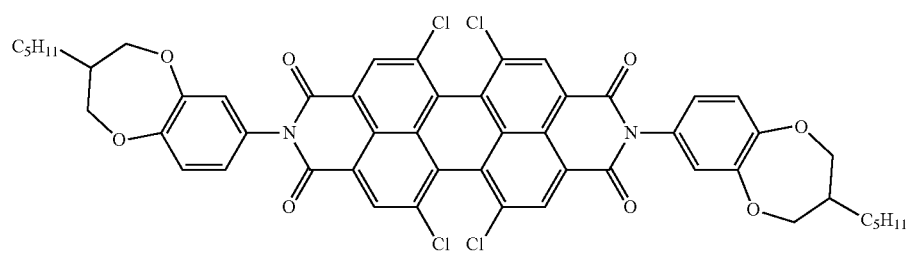

TABLE 2-continued
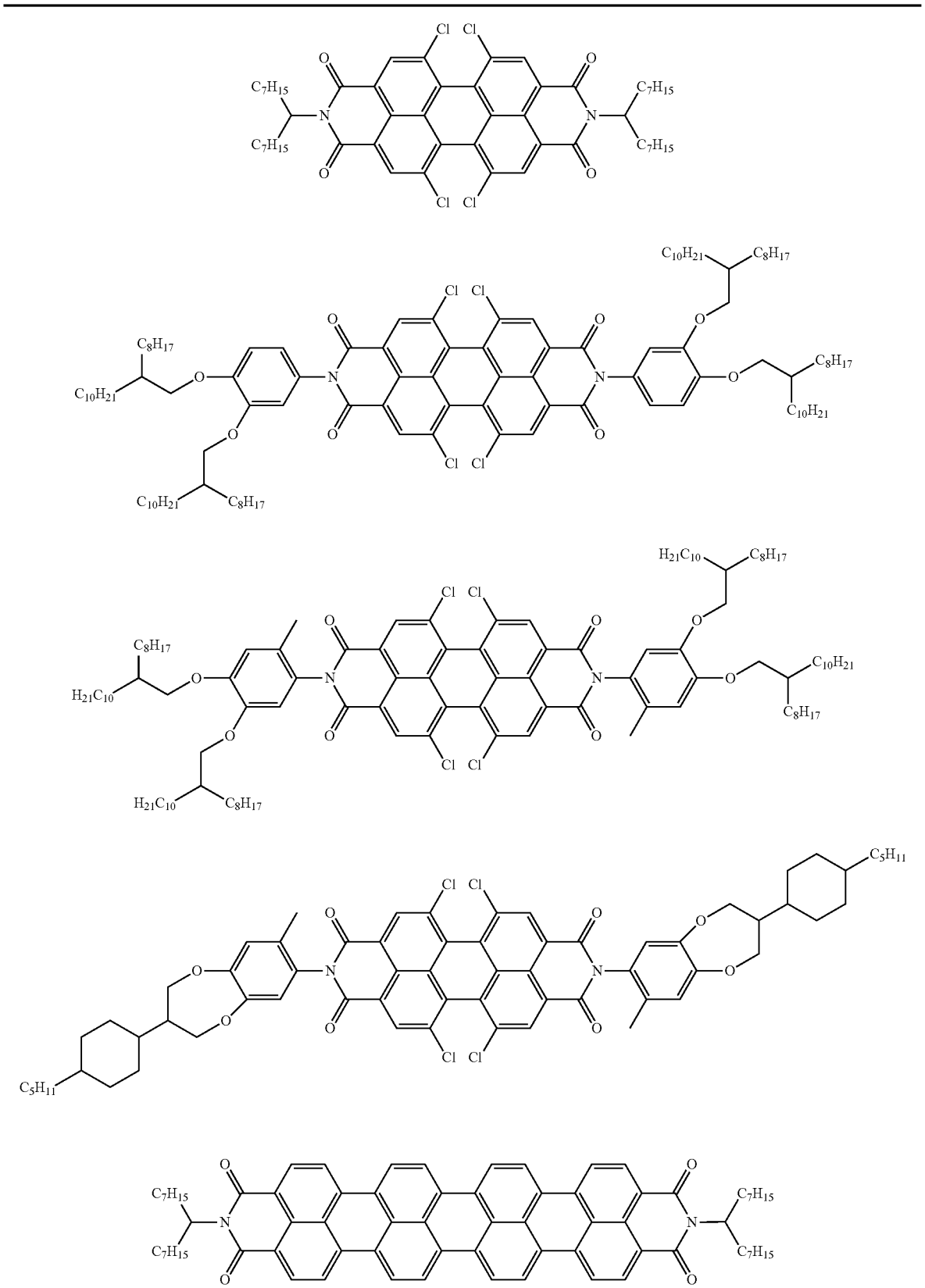

TABLE 2-continued
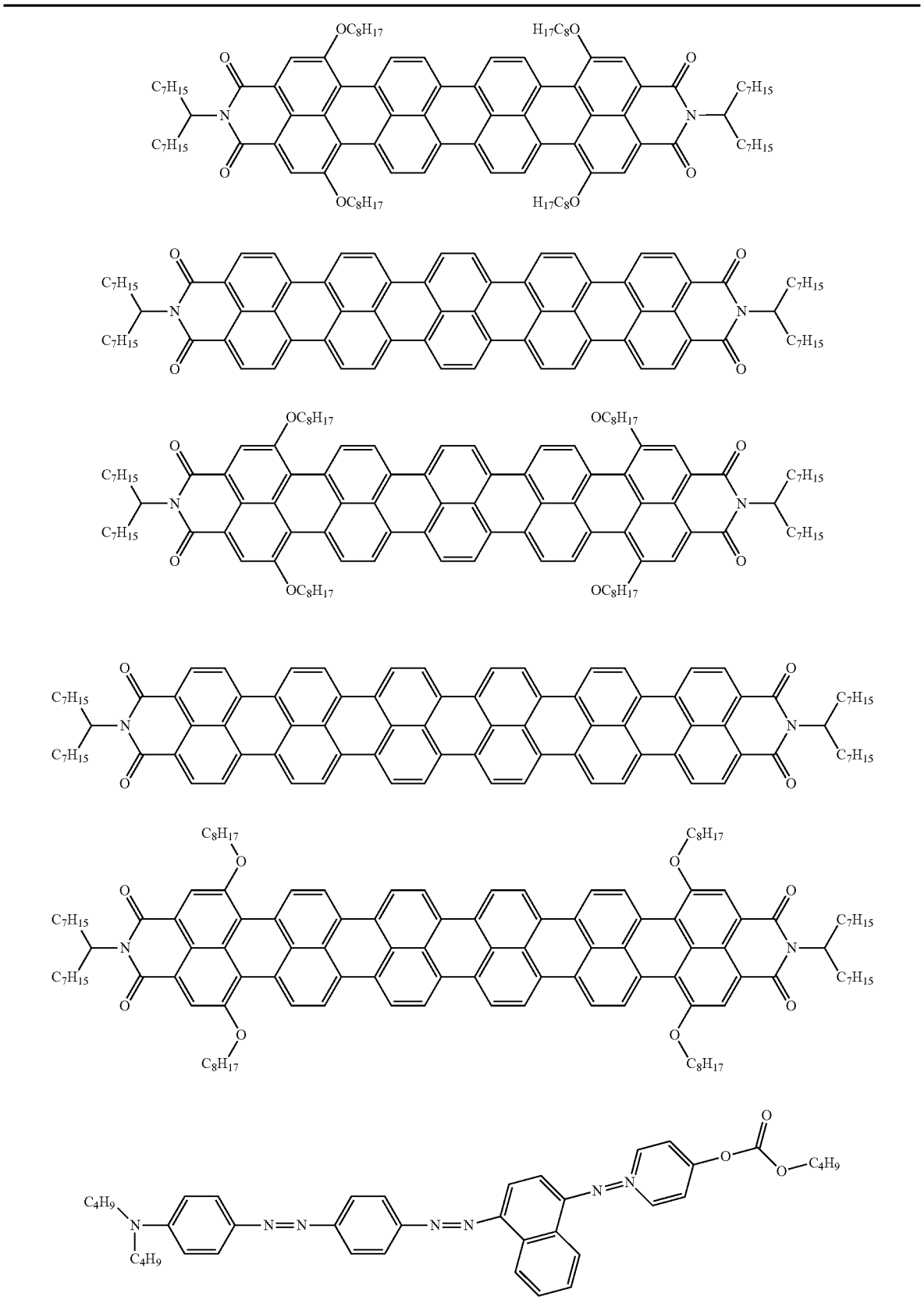

TABLE 2-continued

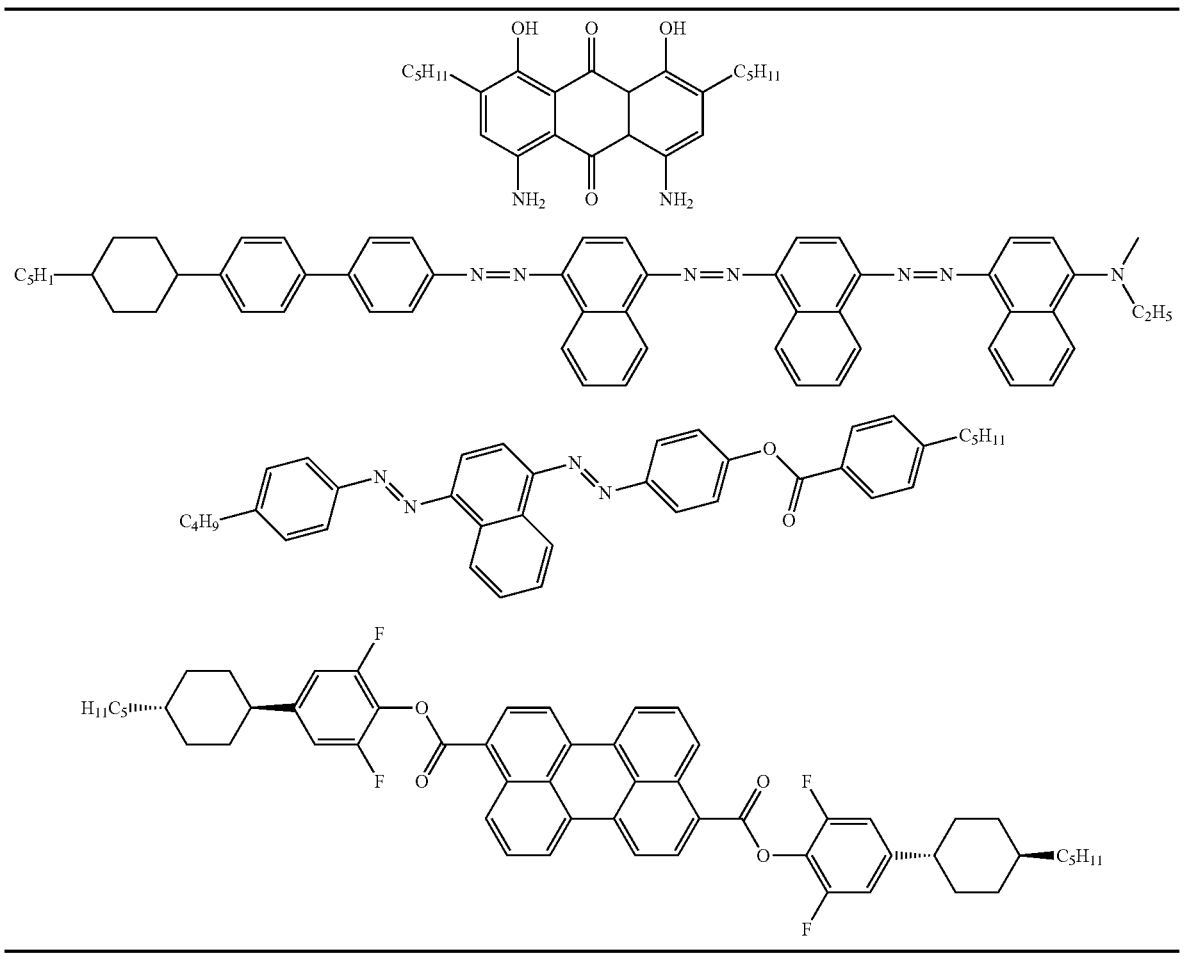

In a preferred embodiment, the switching layer of the device according to the invention comprises one or more quencher compounds. This is particularly preferred if the device according to the invention comprises one or more fluorescent dyes in its switching layer.

Quencher compounds are compounds which quench the fluorescence. The quencher compounds can take on the electronic excitation energy of adjacent molecules, such as, for example, fluorescent dyes, in the switching layer and undergo a transition into an electronically excited state in the process. The quenched fluorescent dye is thus converted into the electronic ground state and is thus prevented from emitting fluorescence or undergoing a subsequent reaction. The quencher compound itself returns to the ground state through radiation-free deactivation or by emission of light and is again available for further quenching.

The quencher compound may have various functions in the switching layer of the device according to the invention. Firstly, the quencher compound may contribute to extending the lifetime of a dye system, by deactivation of electronic excitation energy. Secondly, the quencher compound eliminates additional colour effects which may be aesthetically undesired, for example coloured emission in the inside space emanating from the fluorescent dyes in the switching layer.

In order to achieve effective quenching, the quencher compound should be adapted to the respective dye system, in particular the dye absorbing at the longest wavelength in a dye combination. The way to do this is known to the person skilled in the art.

Preferred quencher compounds are described, for example, in Table 8.1 on page 279 in Joseph R. Lakowicz, Principles of Fluorescence Spectroscopy, $3^{rd}$ Edition, 2010, ISBN 10: 0-387-31278-1, Verlag Springer Science+Business Media LLC. Further classes of molecule are familiar to the person skilled in the art, for example under the key words dark quencher or black hole quencher. Examples are azo dyes and aminoanthraquinones. The quencher compounds used in the switching layer of the device according to the invention may also be non-fluorescent dyes or dyes which only fluoresce in the NIR.

In a preferred embodiment of the switching layer according to the invention, any quencher compounds present are selected so that fluorescence in the visible part of the spectrum is suppressed.

The device according to the invention is preferably suitable for regulating the passage of energy in the form of light emitted by the sun from the environment into an inside space. The passage of energy to be regulated here takes place from the environment (the outside space) into an inside space.

The inside space here can be any desired space that is substantially sealed off from the environment, for example a building, a vehicle or a container.

The invention therefore furthermore relates to the use of the device for regulating the passage of energy from an outside space into an inside space.

However, the device can also be employed for aesthetic room design, for example for light and colour effects. For example, door and wall elements containing the device according to the invention in grey or in colour can be switched to transparent. Furthermore, the device may also comprise white or coloured flat backlighting which is modulated in brightness or yellow flat backlighting which is modulated in colour by means of a blue guest-host display. One or both glass sides of the device according to the invention may be provided with roughened or structured glass for the coupling-out of light and/or for the generation of light effects.

In a further alternative use, the device is employed for regulating the incidence of light on the eyes, for example in protective goggles, visors or sunglasses, where the device keeps the incidence of light on the eyes low in one switching state and reduces the incidence of light less in another switching state.

The device according to the invention is preferably arranged in an opening in a relatively large two-dimensional structure, where the two-dimensional structure itself only allows slight passage of energy, or none at all, and where the opening has relatively high energy transmissivity. The two-dimensional structure is preferably a wall or another boundary of an inside space to the outside. Furthermore, the two-dimensional structure preferably covers an area of at least equal size, particularly preferably an area at least twice as large as the opening in it in which the device according to the invention is arranged.

The device is preferably characterised in that it has an area of at least 0.05 $m^2$, preferably at least 0.1 $m^2$, particularly preferably at least 0.5 $m^2$ and very particularly preferably at least 0.8 $m^2$.

The device is preferably accommodated in an opening having relatively high energy transmissivity, as described above, in a building, a container, a vehicle or another substantially closed space. The device can generally be used for any desired inside spaces, particularly if they have only limited exchange of air with the environment and have light-transmitting boundary surfaces through which input of energy from the outside in the form of light energy can take place. The use of the device for inside spaces which are subjected to strong insolation through light-transmitting areas, for example through window areas, is particularly relevant.

The device according to the invention is switchable. Switching here is taken to mean a change in the passage of energy through the device. The device according to the invention is preferably electrically switchable, as described, for example, in WO 2009/141295 and in the as yet unpublished application EP 12008320.9.

However, it may also be thermally switchable, as described, for example, in WO 2010/118422. In this case, the switching preferably takes place through a transition from a nematic state to an isotropic state through a change in the temperature of the switching layer comprising the compound of the formula (I) or formula (II) and a liquid-crystalline medium. In the nematic state, the molecules of the liquid-crystalline medium are in ordered form and thus so is the compound of the formula (I) or formula (II), for example aligned parallel to the surface of the device through the action of an alignment layer. In the isotropic state, the molecules are in unordered form, and thus so is the compound of the formula (I) or formula (II). The difference between ordered and unordered presence of the dichroic compound of the formula (I) or formula (II) causes a difference in the light transmissivity of the switching layer of the device according to the invention, in accordance with the principle that dichroic compounds have a higher or lower absorption coefficient depending on the alignment in relation to the plane of vibration of the light.

If the device is electrically switchable, it preferably comprises two or more electrodes, which are installed on both sides of the switching layer. The electrodes preferably consist of ITO or a thin, preferably transparent metal and/or metal-oxide layer, for example silver or FTO (fluorine-doped tin oxide) or an alternative material known to the person skilled in the art for this use. The electrodes are preferably provided with electrical connections. The voltage is preferably provided by a battery, a rechargeable battery or an external power supply.

The switching operation in the case of electrical switching takes place through an alignment of the molecules of the liquid-crystalline medium by the application of voltage.

In a preferred embodiment, the device is converted from a state having high absorption, i.e. low light transmissivity, which is present without voltage, into a state having lower absorption, i.e. higher light transmissivity. The liquid-crystalline medium of the switching layer is preferably nematic in both states. The voltage-free state is preferably characterised in that the molecules of the liquid-crystalline medium, and thus the molecules of the compound of the formula (I) or formula (II), are aligned parallel to the plane of the switching layer. This is preferably achieved by a correspondingly selected alignment layer. The state under voltage is preferably characterised in that the molecules of the liquid-crystalline medium, and thus the molecules of the compound of the formula (I) or formula (II), are perpendicular to the plane of the switching layer.

In an alternative embodiment to the embodiment mentioned above, the device is converted from a state having low absorption, i.e. high light transmissivity, which is present without voltage, into a state having higher absorption, i.e. lower light transmissivity. The liquid-crystalline medium of the switching layer is preferably nematic in both states. The voltage-free state is preferably characterised in that the molecules of the liquid-crystalline medium of the switching layer, and thus the molecules of the compound of the formula (I) or formula (II), are aligned perpendicular to the plane of the switching layer. This is preferably achieved by a correspondingly selected alignment layer. The state under voltage is preferably characterised in that the molecules of the liquid-crystalline medium of the switching layer, and thus the molecules of the compound of the formula (I) or formula (II), are parallel to the plane of the switching layer.

According to a preferred embodiment of the invention, the device can be operated without an external power supply by providing the energy required by means of a solar cell or another device for conversion of light and/or heat energy into electrical energy which is connected to the device. The provision of the energy by means of the solar cell can take place directly or indirectly, i.e. via a battery or rechargeable battery or other unit for the storage of energy connected in-between. The solar cell is preferably mounted on the outside of the device or is an internal component of the device, as disclosed, for example, in WO 2009/141295. Particular preference is given here to solar cells which are particularly efficient in the case of diffuse light, and transparent solar cells.

The device according to the invention preferably has the following layer sequence, where further layers may additionally be present. The layers indicated below are preferably directly adjacent to one another in the device:

substrate layer, preferably comprising glass or polymer
electrically conductive transparent layer, preferably comprising ITO
alignment layer
switching layer comprising one or more compounds of the formula (I) or formula (II)
alignment layer
electrically conductive transparent layer, preferably comprising ITO
substrate layer, preferably comprising glass or polymer The preferred embodiments of the individual layers are described below.

The device according to the invention preferably comprises one or more, particularly preferably two, alignment layers. The alignment layers are preferably directly adjacent to the two sides of the switching layer comprising the compound of the formula (I) or formula (II).

The alignment layers used in the device according to the invention can be any desired layers known to the person skilled in the art for this purpose. Preference is given to polyimide layers, particularly preferably layers comprising rubbed polyimide. Polyimide rubbed in a certain manner known to the person skilled in the art results in alignment of the molecules of the liquid-crystalline medium in the rubbing direction if the molecules are parallel to the alignment layer (planar alignment). It is preferred here for the molecules of the liquid-crystalline medium not to be completely planar on the alignment layer, but instead to have a slight pretilt angle. In order to achieve vertical alignment of the compounds of the liquid-crystalline medium to the surface of the alignment layer (homeotropic alignment), polyimide treated in a certain manner is preferably employed as material for the alignment layer (polyimide for very high pretilt angles). Furthermore, polymers obtained by an exposure process to polarised light can be used as alignment layer in order to achieve alignment of the compounds of the liquid-crystalline medium in accordance with an alignment axis (photoalignment).

The switching layer in the device according to the invention is furthermore preferably arranged between two substrate layers or enclosed thereby. The substrate layers can consist, for example, of glass or a polymer, preferably a light-transmitting polymer.

The device is preferably characterised in that it does not comprise a polymer-based polariser, particularly preferably does not comprise a polariser in the solid material phase and very particularly preferably comprises no polariser at all.

However, in accordance with an alternative embodiment, the device may also comprise one or more polarisers. The polarisers in this case are preferably linear polarisers.

If precisely one polariser is present, its absorption direction is preferably perpendicular to the orientation axis of the compounds of the liquid-crystalline medium of the device according to the invention on the side of the switching layer on which the polariser is located.

In the device according to the invention, both absorptive and also reflective polarisers can be employed. Preference is given to the use of polarisers which are in the form of thin optical films. Examples of reflective polarisers which can be used in the device according to the invention are DRPF (diffusive reflective polariser film, 3M), DBEF (dual brightness enhanced film, 3M), DBR (layered-polymer distributed Bragg reflectors, as described in U.S. Pat. No. 7,038,745 and U.S. Pat. No. 6,099,758) and APF films (advanced polariser film, 3M, cf. Technical Digest SID 2006, 45.1, US 2011/0043732 and U.S. Pat. No. 7,023,602). It is furthermore possible to employ polarisers based on wire grids (WGPs, wire-grid polarisers) which reflect infrared light. Examples of absorptive polarisers which can be employed in the devices according to the invention are the Itos XP38 polariser film and the Nitto Denko GU-1220DUN polariser film. An example of a circular polariser which can be used in accordance with the invention is the APNCP37-035-STD polariser (American Polarizers). A further example is the CP42 polariser (ITOS).

The device according to the invention furthermore preferably comprises an optical waveguide system which transports the light to a solar cell or another device for the conversion of light and/or heat energy into electrical energy, preferably as described in WO 2009/141295. The optical waveguide system collects and concentrates light hitting the device. It preferably collects and concentrates light emitted by fluorescent dichroic dyes in the switching layer. The optical waveguide system is in contact with a device for the conversion of light energy into electrical energy, preferably a solar cell, so that the collected light hits the latter in concentrated form. In a preferred embodiment of the invention, the device for the conversion of light energy into electrical energy is mounted at the edge of the device, integrated into the latter and electrically connected to means for the electrical switching of the device according to the invention.

In a preferred embodiment, the device according to the invention is a constituent of a window, particularly preferably a window comprising at least one glass surface, very particularly preferably a window which comprises multi-pane insulating glass.

Window here is taken to mean, in particular, a structure in a building which comprises a frame and at least one glass pane surrounded by this frame. It preferably comprises a heat-insulating frame and two or more glass panes (multi-pane insulating glass).

According to a preferred embodiment, the device according to the invention is applied directly to a glass surface of a window, particularly preferably in the interspace between two glass panes of multipane insulating glass.

The invention furthermore relates to a window comprising a device according to the invention, preferably having the preferred features indicated above.

WORKING EXAMPLES

The following examples are intended to illustrate the present invention and should not be interpreted as restrictive.

In the present application, structures of liquid-crystalline compounds are reproduced by means of abbreviations (acronyms). These abbreviations are explicitly presented and explained in WO 2012/052100 (pp. 63-89).

All physical properties are determined in accordance with "Merck Liquid Crystals, Physical Properties of Liquid Crystals", Status November 1997, Merck KGaA, Germany, and apply for a temperature of 20° C. The value of Δn is determined at 589 nm, and the value of Δε is determined at 1 kHz, unless explicitly indicated otherwise in each case. $n_e$ and $n_o$ are in each case the refractive indices of the extraordinary and ordinary light beam under the conditions indicated above.

The degree of anisotropy R is determined from the value for the extinction coefficient E(p) (extinction coefficient of the mixture in the case of parallel alignment of the molecules to the polarisation direction of the light) and the value for the extinction coefficient of the mixture E(s) (extinction coefficient of the mixture in the case of perpendicular alignment of the molecules to the polarisation direction of the light), in each case at the wavelength of the maximum of the absorption band of the dye in question. If the dye has a plurality of absorption bands, the strongest absorption band is selected. The alignment of the molecules of the mixture is achieved by an alignment layer, as known to the person skilled in the art in the area of LC display technology. In order to eliminate influences by liquid-crystalline medium, other absorptions and/or reflections, each measurement is carried out against an identical mixture comprising no dye, and the value obtained is subtracted.

The measurement is carried out using linear-polarised light whose vibration direction is either parallel to the alignment direction (determination of E(p)) or perpendicular to the alignment direction (determination of E(s)). This can be achieved by a linear polariser, where the polariser is rotated with respect to the device in order to achieve the two different vibration directions. The measurement of E(p) and E(s) is thus carried out via the rotation of the vibration direction of the incident polarised light.

The degree of anisotropy R is calculated from the resultant values for E(s) and E(p) in accordance with the formula $$R=[E(p)-E(s)]/[E(p)+2*E(s)],$$

as indicated, inter alia, in "Polarized Light in Optics and Spectroscopy", D. S. Kliger et al., Academic Press, 1990. A detailed description of the method for the determination of the degree of anisotropy of liquid-crystalline media comprising a dichroic dye is also given in B. Bahadur, Liquid Crystals—Applications and Uses, Vol. 3, 1992, World Scientific Publishing, Section 11.4.2.

A) Preparation of the Dyes

A-1) Synthesis of Compound BT-1

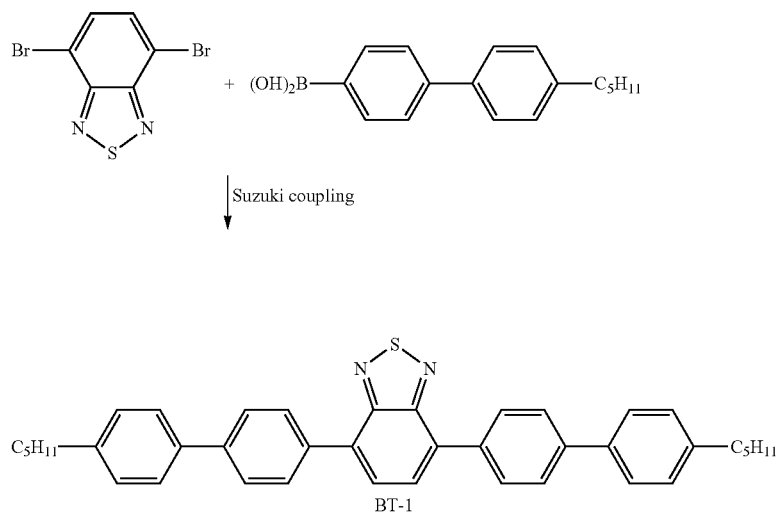

The dibromide (5.0 mmol) and the boronic acid (10.0 mmol) are initially introduced in 40 ml of toluene under nitrogen. 20.1 ml of a 2.0 mol/l solution of sodium carbonate are subsequently added. Tris(dibenzylideneacetone)dipalladium (0.05 mmol) and tris-(o)-tolylphosphine (0.2 mmol) are subsequently added, and the mixture is stirred under reflux overnight. The batch is subsequently allowed to cool to 40° C., and the aqueous phase is separated off. The aqueous phase is extracted with warm toluene. The combined organic phases are concentrated and eluted over silica gel with toluene. The product is subsequently recrystallised from isopropanol/toluene 1:4, giving the product in a yield of 54% of theory. The identity of the product is confirmed by mass spectroscopy (m/e=580).

A-2) Synthesis of Compound BT-2

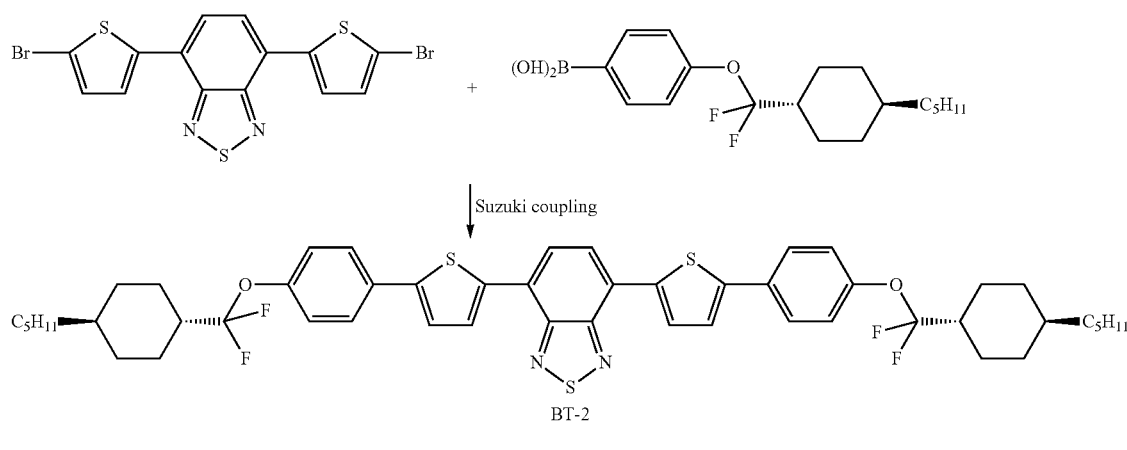

The compound is synthesised by the procedure indicated in the case of A-1), with the difference that the mixture is heated under reflux for only 1.5 h before being worked up. The recrystallisation is carried out from toluene. The product is obtained as powder in a yield of 29.5% of theory, the purity according to HPLC is 100%. The identity of the product is confirmed by mass spectroscopy (m/e=888).

A-3) Synthesis of Compound BT-3

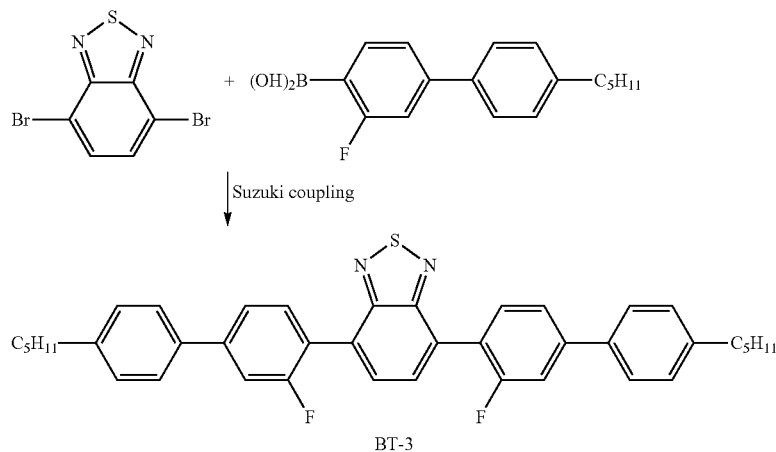

The compound is synthesised by the procedure indicated in the case of A-1). The recrystallisation is carried out from isopropanol/toluene 1:1. The product is obtained as crystals in a yield of 45.1% of theory, the purity according to HPLC is 99.4%. The identity of the product is confirmed by mass spectroscopy (m/e=616).

A-4) Preparation of Compound BT-4

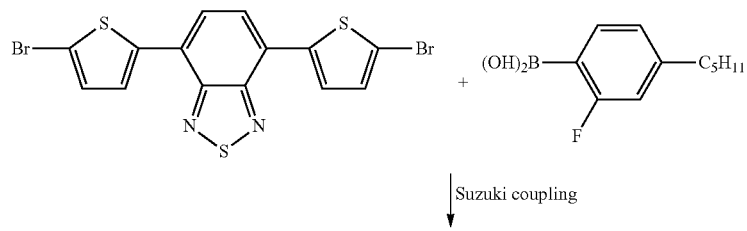

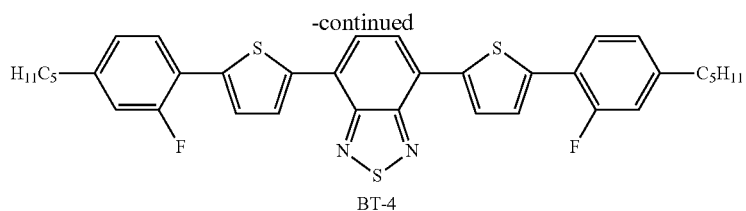

BT-4

The compound is synthesised by the procedure indicated in the case of A-1), with the difference that 0.3 eq. of aliquot 336 is added together with the carbonate solution and the recrystallisation is carried out from toluene. The product is obtained in a yield of 68.5% of theory, the purity according to HPLC is 99.6%. The identity of the product is confirmed by mass spectroscopy (m/e=628).

A-5) Preparation of Compound BT-5

Steps 1 and 2:

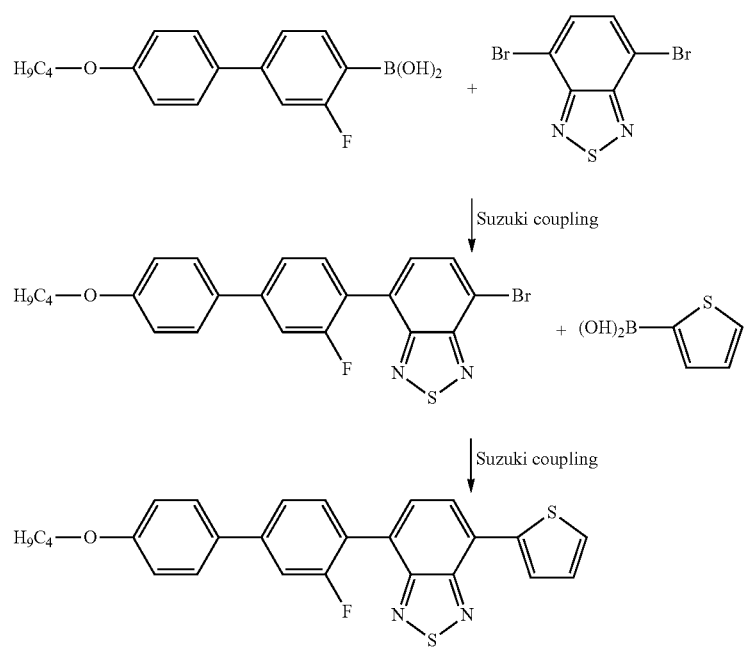

Steps 3 and 4:

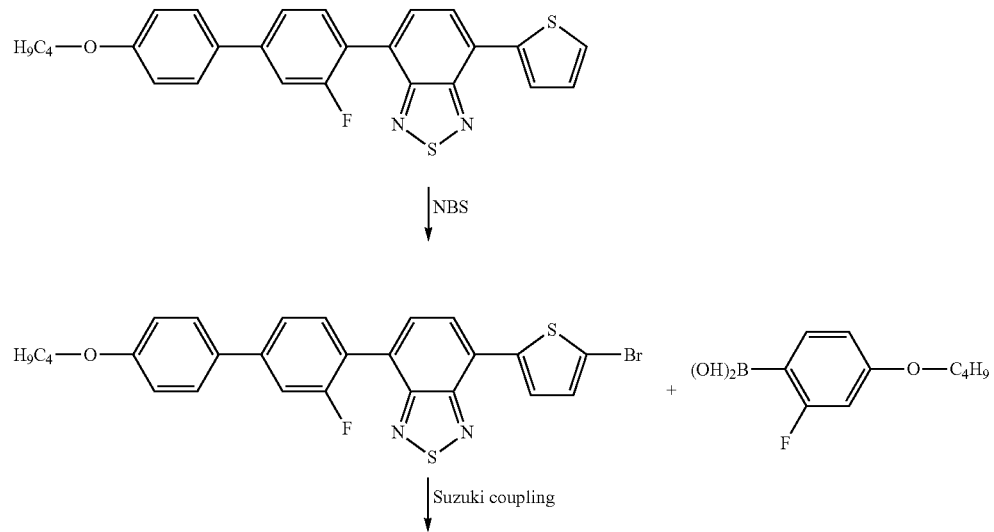

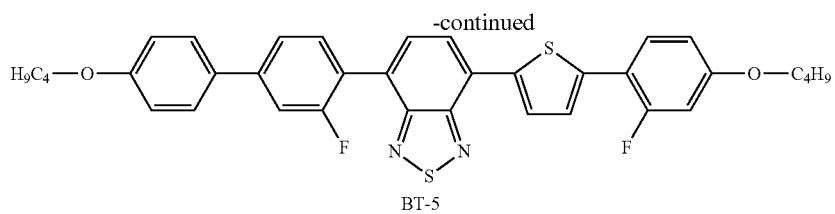

BT-5

Step 1:

The dibromide (33.8 mmol) and the boronic acid (33.8 mmol) are initially introduced in 40 ml of toluene under nitrogen. 67.7 ml of a 2.0 mol/l solution of sodium carbonate are subsequently added. Tris(dibenzylideneacetone)dipalladium (0.34 mmol) and tris-(o)-tolylphosphine (1.35 mmol) are subsequently added, and the mixture is stirred under reflux overnight. The batch is subsequently allowed to cool, and the aqueous phase is separated off. The aqueous phase is extracted with warm toluene. The combined organic phases are evaporated to dryness. The product is eluted over silica gel with 1-chlorobutane. The product is then recrystallised from chlorobutane. The product is obtained in a yield of 38.7% of theory and purity of 99.8% (HPLC). The identity of the product is confirmed by mass spectroscopy (m/e=620).

Step 2:

Sodium metaborate tetrahydrate (45.8 mmol) is initially introduced in 30 ml of water. Bistriphenylphosphinepalladium(II) chloride (0.5 mmol), hydrazinium hydroxide (0.89 mmol) and the boronic acid (14.4 mmol) and THF (80 ml) are then added, and the mixture is stirred for 5 min. The bromide (13.1 mmol) is then added, and the mixture is heated under reflux for 3 h. Water and methyl tert-butyl ether are subsequently added to the mixture, which is then subjected to aqueous work-up. After the organic phases have been evaporated to dryness, the product is obtained in a yield of 90.9% of theory and a purity of 97.9% (HPLC). The identity of the product is confirmed by mass spectroscopy (m/e=460).

Step 3:

The thiophene derivative (11.9 mmol) is dissolved in 60 ml of 1,2-dichlorobenzene under $N_2$. N-Bromosuccinimide (12.5 mmol) is added with stirring, and the mixture is heated to 70° C. The mixture is subsequently left to stir at this temperature for 4 h. The mixture is allowed to cool, 0.5 M NaOH solution is then added, and the mixture is stirred for 30 min. The precipitated solid is isolated and dried. The product is obtained in a yield of 87.8% of theory and purity of 97.4% (HPLC).

Step 4:

The bromide (4.5 mmol) and the boronic acid (4.9 mmol) are initially introduced in 50 ml of toluene under nitrogen. 9.0 ml of a 2.0 mol/l solution of sodium carbonate are subsequently added. Tris(dibenzylideneacetone)dipalladium (0.045 mmol) and tris-(o)-tolylphosphine (0.18 mmol) are subsequently added, and the mixture is stirred under reflux overnight. The batch is subsequently allowed to cool to 40° C., and the aqueous phase is separated off. The aqueous phase is extracted with warm toluene. The combined organic phases are concentrated and eluted over silica gel with chlorobutane. The product is subsequently recrystallised from chlorobutane, giving the product in a yield of 61% of theory.

A-6) Preparation of Compounds BT-6 to BT-17

Compounds BT-6 to BT-17 can be prepared correspondingly. Their structures are shown in Table 3 below.

A-7) Preparation of Compound BT-18

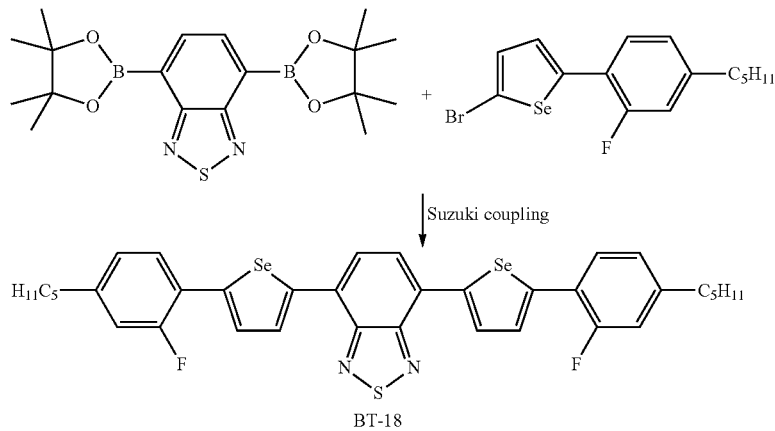

BT-18

The diboronic ester (11.9 mmol) was initially introduced in 150 ml of toluene under nitrogen and warmed to 60°. The corresponding bromide (29.7 mmol) was dissolved in 50 ml of toluene, which had likewise been warmed to 60°, and added. The 2 molar sodium carbonate solution (94.8 mmol) which had previously been warmed to 40° was then added rapidly. 0.95 mmol of tris(dibenzylideneacetone)dipalladium and 0.24 mmol of tris-(o)-tolylphosphine were then added and rapidly brought to the reflux temperature. The mixture was boiled under reflux overnight. The mixture was cooled to 40°, the aqueous phase was separated off, the org. phase was washed 1× with saturated NaCl solution. The org. extract was then concentrated and chromatographed over 11111silica gel with a mixture of toluene/heptane (1:1). The collected fractions were subsequently evaporated to dryness and recrystallised a number of times from toluene, giving 379 mg of product (4.2% of theory). The identity was confirmed by mass spectroscopy (M:722.65) and NMR.

A-8) Preparation of Compound BT-19

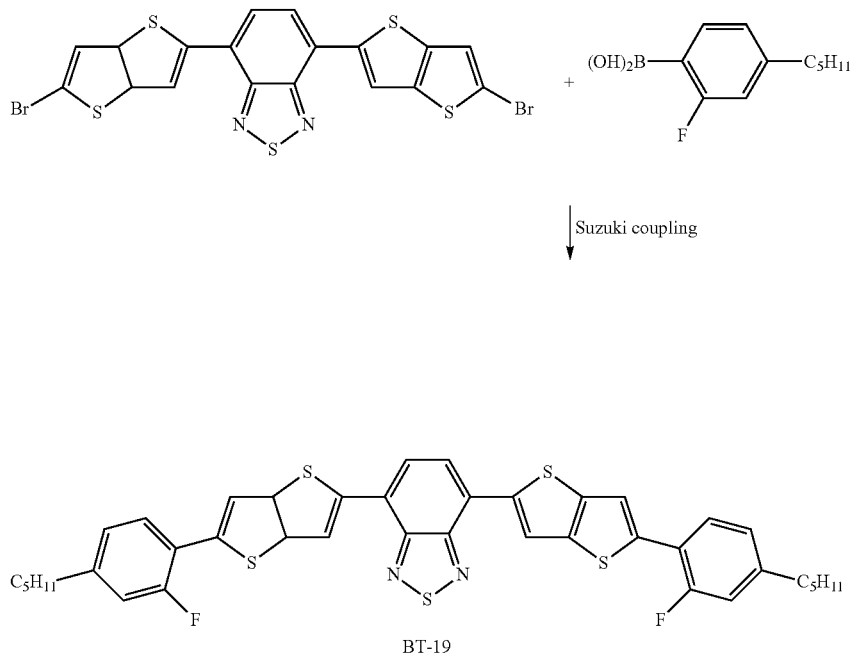

BT-19

Compound BT-19 is synthesised by the procedure indicated in the case of A-1). The identity of the product is confirmed by mass spectroscopy (m/e=741).

A-9) Preparation of Compound BT-20

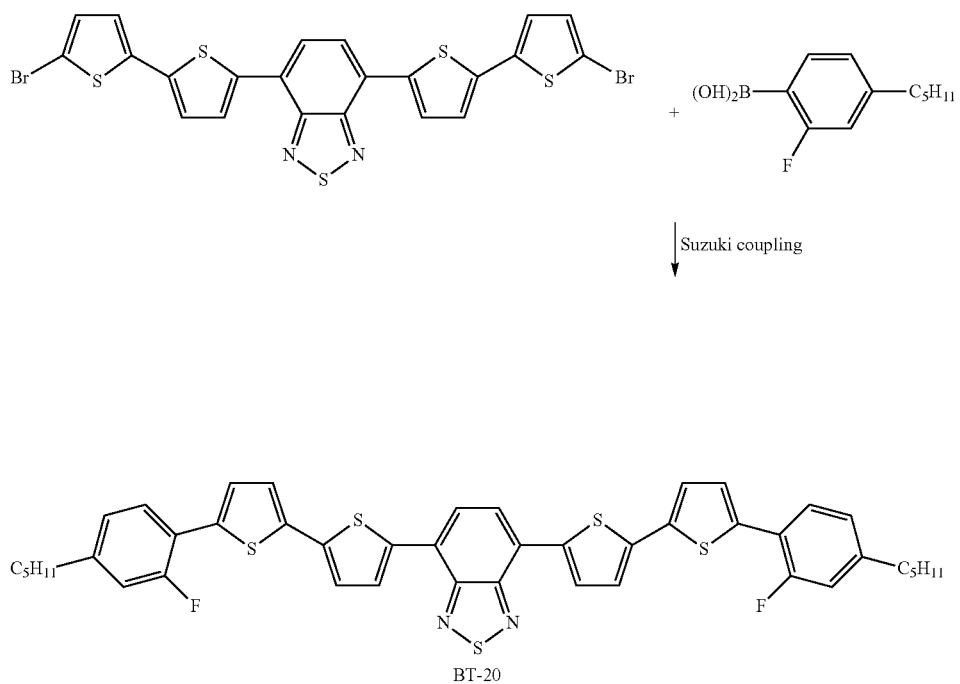

BT-20

Compound BT-20 is synthesised by the procedure indicated in the case of A-1). The identity of the product is confirmed by mass spectroscopy (m/e=793).

A-10) Preparation of Compound BT-21

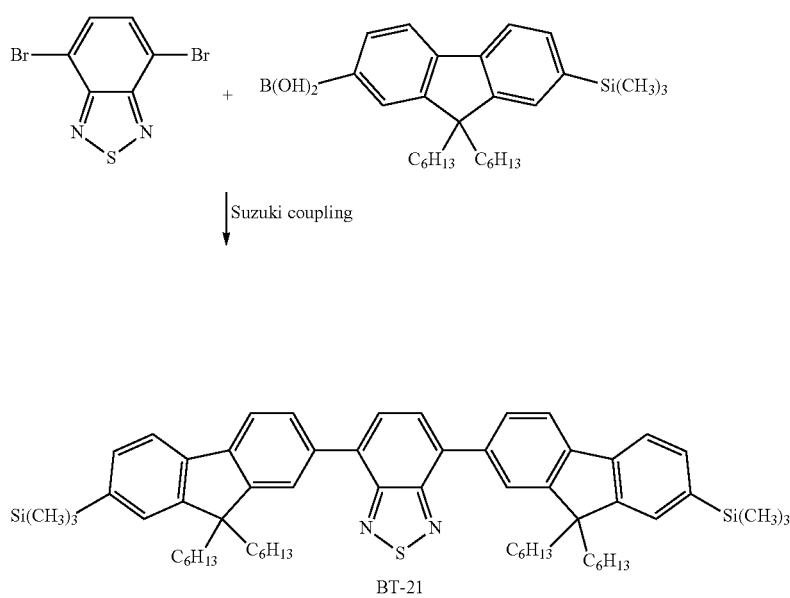

BT-21

Compound BT-21 is synthesised by the procedure indicated in the case of A-1). The identity of the product is confirmed by mass spectroscopy (m/e=945).

A-11) Preparation of Compound BT-22

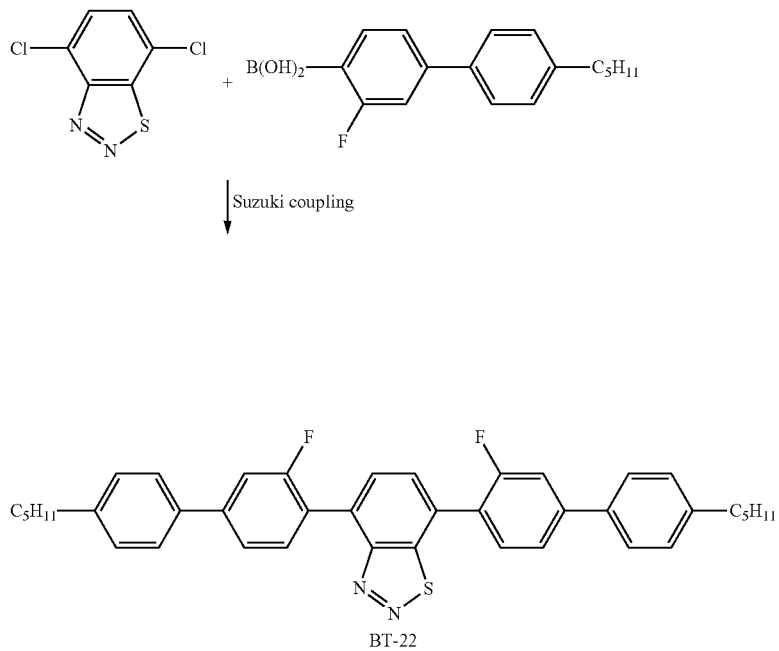

BT-22

The dichloride (5.0 mmol) and the boronic acid (10.0 mmol) are initially introduced in 40 ml of toluene under nitrogen. 20.1 ml of a 2.0 mol/lsolution of sodium tert-butoxide are subsequently added. Tris(dibenzylideneacetone)dipalladium (0.05 mmol) and tricyclohexylphosphine (0.2 mmol) are subsequently added, and the mixture is stirred under reflux overnight. The batch is subsequently allowed to cool to 40° C. and is subjected to aqueous work-up. The combined organic phases are concentrated and eluted over silica gel with toluene. The product is subsequently recrystallised from isopropanol/toluene 1:4, giving the product in a yield of 4.5% of theory. The identity of the product is confirmed by mass spectroscopy (m/e=616).

TABLE 3
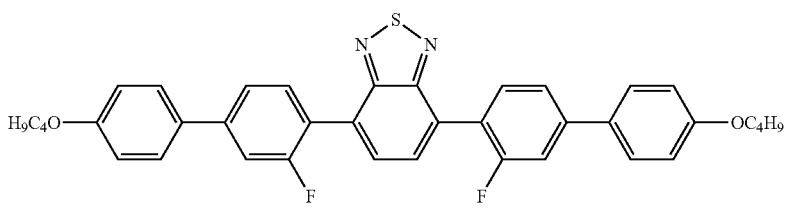 BT-6
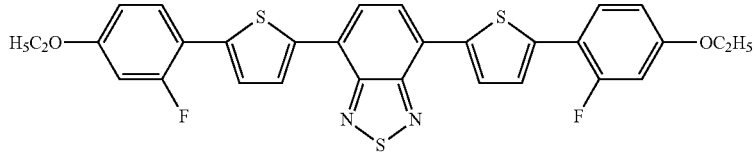 BT-7
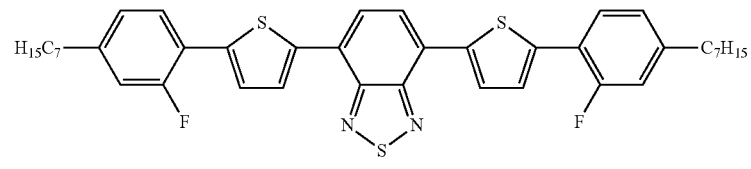 BT-8
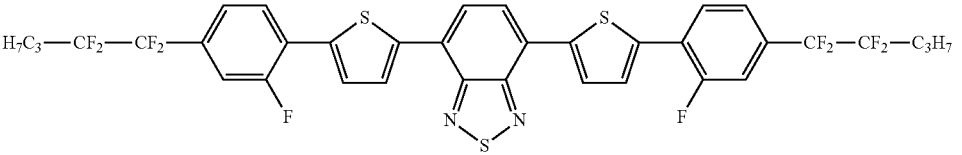 BT-9
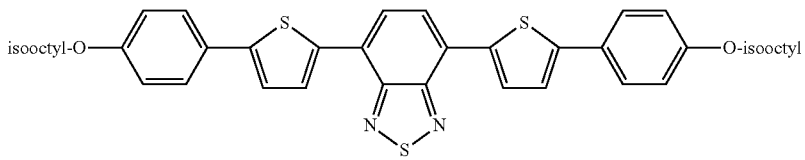 BT-10
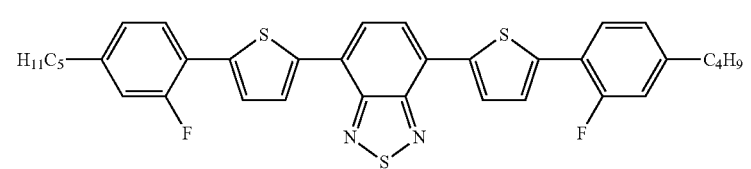 BT-11
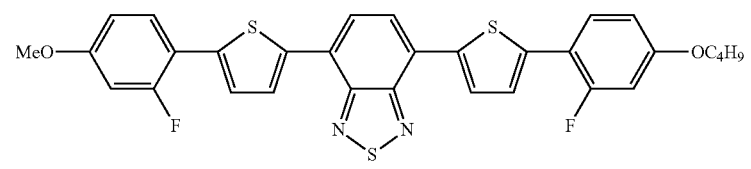 BT-12
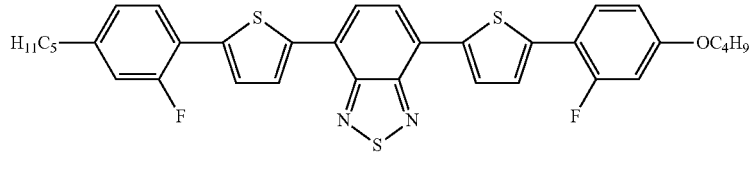 BT-13
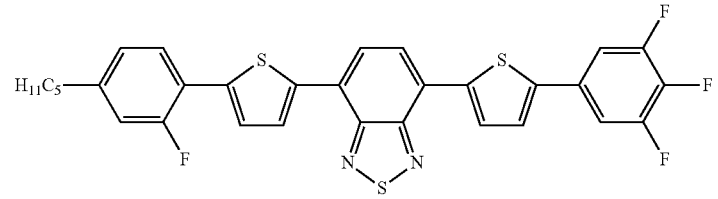 BT-14

TABLE 3-continued
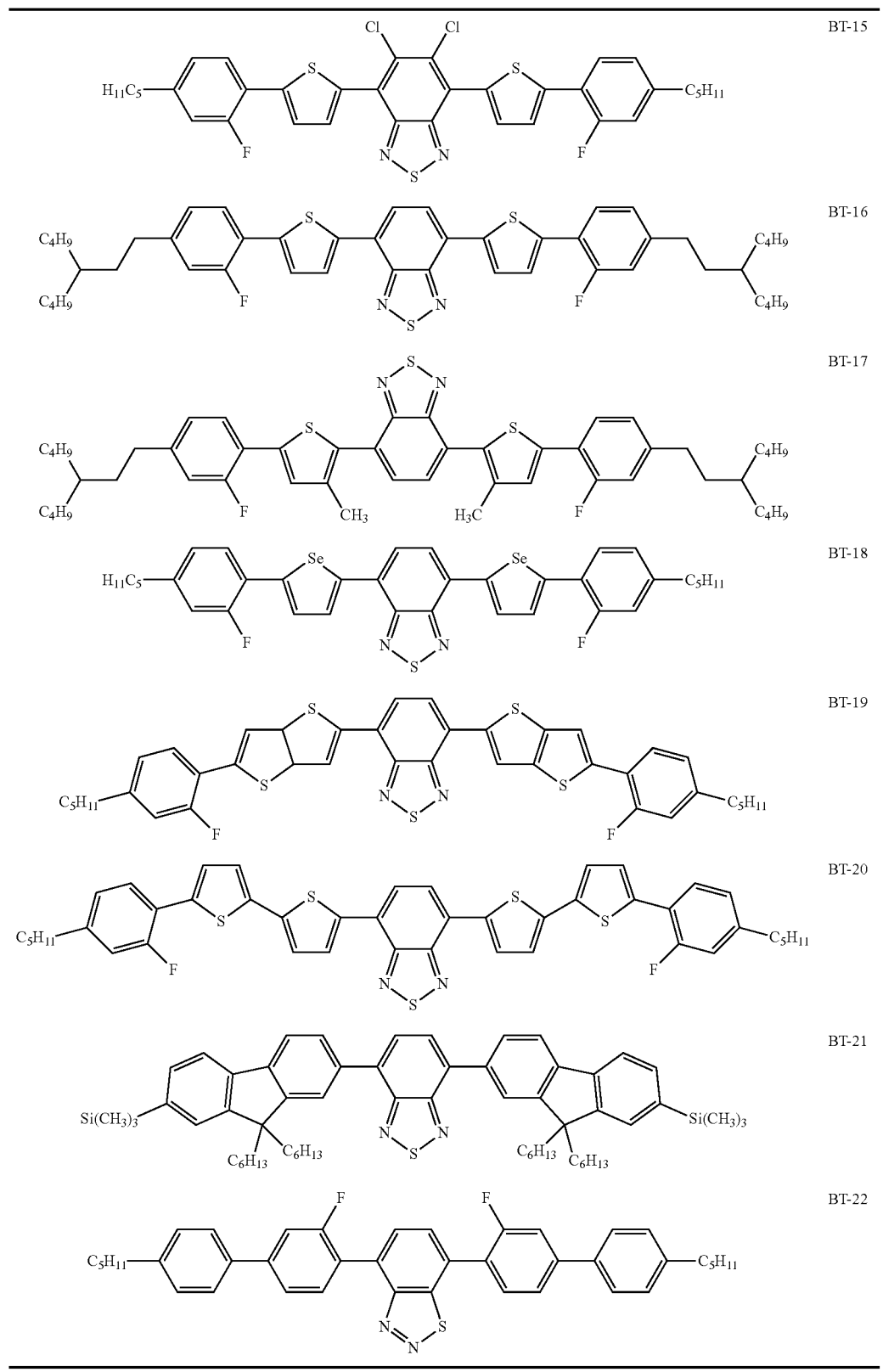
B) Determination of the Properties of the Dyes
The dyes prepared are investigated with respect to their physical properties in order to establish their suitability for use in devices for regulating the transmission of energy. For comparison, the corresponding properties are indicated for compound D-3 (structure see below).

The light stability is determined as follows: a UV-VIS spectrum is recorded in a sealed measurement cell at the beginning of the exposure. The sample is then exposed by subjecting it to intense light (exclusion of UV light by 400 nm cut-off filter) in an MTS-Atlas Suntest CPS+. A further spectrum is recorded at regular intervals. The time after which the absorbance value of the longest-wavelength and preferably most intense absorption has dropped to below 80% of the initial value is indicated to denote the light stability.

The Stokes shift indicated is the difference between the wavelength of the shortest-wavelength emission maximum and the wavelength of the longest-wavelength absorption maximum.

TABLE 4

| Name | Absorption maximum/nm | Degree of anisotropy R | Stokes shift/nm | Solubility in M-1 in % by weight | Light stability |
|---|---|---|---|---|---|
| BT-1 | 413 | 0.80 | not determ. | >0.50 | 2 weeks |
| BT-2 | 502 | 0.74 | 115 | 0.30 | 32 weeks |
| BT-3 | 390 | 0.80 | not determ. | >0.50 | 1 week |
| BT-4 | 505 | 0.71 | 125 | 0.75 | 39 weeks |
| BT-5 | 459 | 0.77 | not determ. | 3.90 | 12 weeks |
| BT-6 | 398 | 0.81 | not determ. | <0.25 | <1 week |
| BT-7 | 517 | 0.73 | not determ. | 0.30 | 22 weeks |
| BT-8 | 507 | 0.71 | not determ. | 0.40 | 27 weeks |
| BT-9 | 491 | 0.73 | not determ. | 0.30 | 9 weeks |
| BT-10 | 524 | 0.72 | not determ. | 0.30 | 18 weeks |
| BT-11 | 505 | 0.73 | 120 | 0.25 | 21 weeks |
| BT-12 | 515 | 0.74 | 125 | 0.25 | 25 weeks |
| BT-13 | 510 | 0.76 | 125 | 1.50 | 17 weeks |
| BT-14 | 495 | 0.69 | 120 | 1.60 | 13 weeks |
| BT-15 | 475 | 0.74 | not determ. | 3.80 | 8 weeks |
| BT-16 | 505 | 0.72 | not determ. | not determ. | not determ. |
| BT-17 | 463 | 0.67 | not determ. | not determ. | not determ. |
| BT-18 | 525 | 0.77 | not determ. | not determ. | not determ. |
| D-3 | 590 | 0.68 | 50 | 0.50 | >15 weeks |

The measurements show that the benzothiadiazole compounds according to the invention have excellent properties with respect to degree of anisotropy, solubility in liquid-crystalline media and Stokes shift. Furthermore, the compounds according to the invention, containing at least one sulfur-containing heterocycle bonded directly to the benzothiadiazole radical, have particularly high light stability. Furthermore, they have different absorption colours depending on the substitution pattern, meaning that a mixture comprising just two or more of the dyes according to the invention covers a large part of the visible spectrum. If a red-absorbent dye is added as further dye, a black mixture can be obtained.

The high Stokes shift of the compounds makes it possible to achieve a high fluorescence yield, since only low re-absorption of the fluorescence takes place. This is a major advantage on use of the compounds in devices in which the fluorescence radiation is utilised for the recovery of energy (autonomous devices for regulating energy transmission in windows comprising solar cells, cf. WO 2009/141295).

C) Preparation of Liquid-Crystalline Media Comprising the Dyes

C-1) Preparation of Mixture LC-1

The following dyes in the proportions indicated are added to the base mixture M-1 (see below), and a solution is prepared:

TABLE 5

| Dye | Proportion |
|---|---|
| BT-4 | 0.20% by weight |
| D-1 | 0.49% by weight |
| D-2 | 0.35% by weight |
| D-3 | 0.35% by weight |

Composition of Base Mixture M-1:

TABLE 6

| M-1 | | |
|---|---|---|
| Clearing point | 114.5° C. | |
| Delta-n | 0.1342 | |
| $n_e$ | 1.6293 | |
| $n_o$ | 1.4951 | |
| Composition | Compound | % by weight |
| | CPG-3-F | 5 |
| | CPG-5-F | 5 |
| | CPU-3-F | 15 |
| | CPU-5-F | 15 |
| | CP-3-N | 16 |
| | CP-5-N | 16 |
| | CCGU-3-F | 7 |
| | CGPC-3-3 | 4 |
| | CGPC-5-3 | 4 |
| | CGPC-5-5 | 4 |
| | CCZPC-3-3 | 3 |
| | CCZPC-3-4 | 3 |
| | CCZPC-3-5 | 3 |

Structures of the Other Dyes Used:

TABLE 7

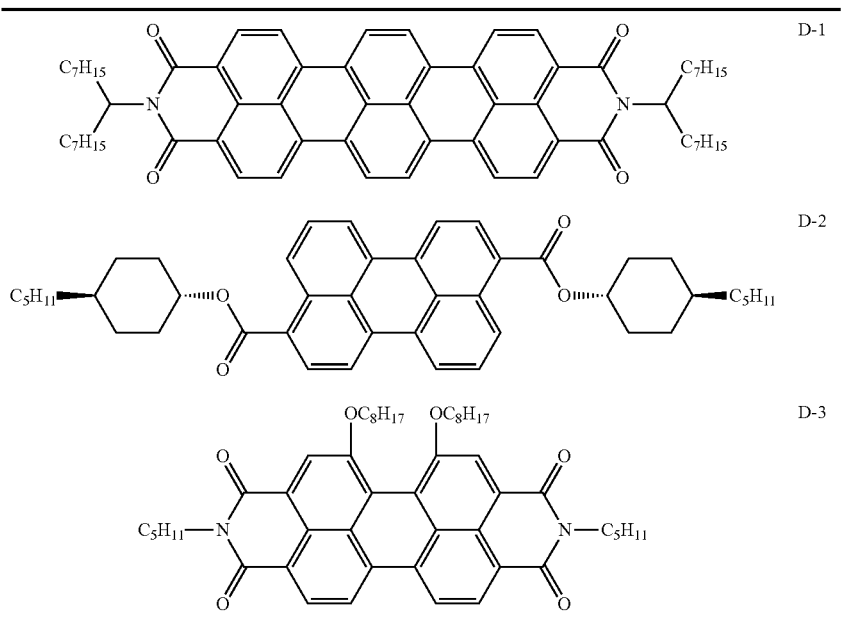

D) Use of Liquid-crystalline Media Comprising the Dyes in Devices for Regulating the Passage of Energy In order to produce the device, the liquid-crystal mixture comprising the dyes (LC-1) is introduced into the interspace of the following layer arrangement:
substrate layer
ITO layer
polyimide alignment layer
interspace kept open using spacers
polyimide alignment layer
ITO layer
substrate layer The liquid-crystal layer in this arrangement is aligned in a planar manner with antiparallel pretilt angle. This alignment is achieved by two polyimide layers rubbed antiparallel to one another. The thickness of the liquid-crystalline layer is defined by spacers and is usually 25 μm.

Values for the degree of light transmission $\tau_v$ for both the dark and bright switching states of the device are determined and are shown below. The bright switching state is achieved by application of a voltage, while the dark switching state is present without voltage. Furthermore, the colour location of the device (in CIE coordinates) in the dark and bright states is determined.

The measurement is carried out with the device comprising the liquid-crystalline medium with dyes in the measurement beam and a device of the same construction correspondingly without the dyes in the reference beam. Reflection and absorption losses of the cell are thereby eliminated.

The value $\tau_v$ and the CIE coordinates (x,y) are defined as follows: $\tau_v$=degree of light transmission, determined in accordance with DIN EN410

The colour location (for white, grey, black) of the basic standard illuminant D65 here is at x=0.3127 and y=0.3290 (Manfred Richter, Einführung in die Farbmetrik [Introduction to Colorimetry], second Edition 1991, ISBN 3-11-008209-8). The colour locations (x,y) indicated all relate to the standard illuminant D65 and the 2° standard observer in accordance with CIE 1931.

Measurement values obtained for the device:
dark state: x=0.312; y=0.324; $\tau_v$=33%
bright state: x=0.319; y=0.336; $\tau_v$=60%

In the example, good stability of the liquid-crystalline medium and adequate solubility of the dyes in the liquid-crystalline medium are apparent.

Furthermore, the example shows that the device can be switched from a dark state having significantly lower light transmission into a bright state having significantly increased light transmission by application of a voltage.

E) Production of Test Devices and Determination of the Relative Fluorescence from Wave Guidance In order to measure the relative fluorescence from wave guidance, a mixture of the respective dye in the liquid-crystalline base mixture M-1 is prepared. The concentration in all cases is selected so that a transmission of 35% through the mixture is obtained. The mixture is introduced into a cell having antiparallel alignment layers (layer thickness 25 microns). The cell is exposed using a halogen lamp (300 W). The amount of light propagated as fluorescence emission by wave guidance is measured individually at the edges parallel and perpendicular to the alignment axis and subsequently averaged. To this end, the light is guided into an Ulbricht sphere and measured using a spectrometer. The area under the emission spectrum is formed and compared with that of reference substance D-3. The comparison is indicated as relative value in percent, which arises from the quotients of the measurement vs. reference areas.

The following values are obtained for the compounds according to the invention mentioned below:

TABLE 8

| Name | Relative fluorescence from wave guidance |
|---|---|
| BT-4 | 108% |
| BT-8 | 106% |
| BT-9 | 110% |
| BT-11 | 111% |

TABLE 8-continued

| Name | Relative fluorescence from wave guidance |
|---|---|
| BT-12 | 113% |
| BT-13 | 113% |
| BT-14 | 111% |

On use in a device for regulating the passage of energy, in which the absorbed light energy is re-emitted via fluorescence, the compounds according to the invention exhibit an excellent fluorescence light yield at the edges of the device. The fluorescence light can thus be absorbed at these points and converted into electrical energy, for example by means of solar cells. In this way, it is possible to obtain devices for regulating the passage of energy which can be switched autonomously, i.e. independently of external supply of energy, since they can utilise absorbed light energy via fluorescence emission and subsequent conversion of the fluorescence light into electrical energy for their own energy supply.

The invention claimed is:

1. A device for regulating the passage of energy in the form of light emitted by the sun from the environment into an inside space, where the device comprises a switching layer comprising one or more dichroic dyes of formula (I)

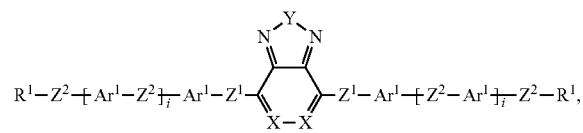

formula (I)

or formula (II)

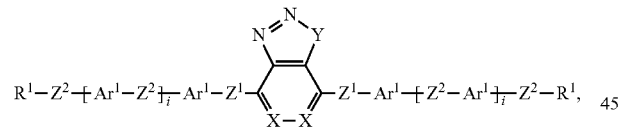

formula (II)

where:
X is on each occurrence, identically or differently, CR$^2$ or N;
Y is equal to S or Se;
Z$^1$ is on each occurrence, identically or differently, a single bond, —CR$^3$=CR$^3$— or —C≡C—;
Z$^2$ is on each occurrence, identically or differently, a single bond, O, S, C(R$^3$)$_2$, —CR$^3$=CR$^3$— or —C≡C—;
Ar$^1$ is on each occurrence, identically or differently, an aryl or heteroaryl group having 5 to 30 aromatic ring atoms, which may be substituted by one or more radicals R$^4$;
R$^1$ is on each occurrence, identically or differently, N(R$^5$)$_2$ or a straight-chain or branched alkyl or alkoxy having 3 to 10 C atoms, which may be substituted by one or more radicals R$^5$, where one or more CH$_2$ groups in the alkyl or alkoxy groups may each be replaced by —O—, —S—, —R$^5$C=CR$^5$—, or a siloxanyl group having 1 to 10 Si atoms, which may be substituted by one or more radicals R$^5$;

R$^2$ is on each occurrence, identically or differently, H, D, F, Cl, CN, —(C=O)OR$^5$, —O(C=O)R$^5$, or an alkyl, alkoxy or thioalkoxy group having 1 to 10 C atoms, which may be substituted by one or more radicals R$^5$, where one or more CH$_2$ groups in the alkyl, alkoxy or thioalkoxy groups may each be replaced by —R$^5$C=CR$^5$—, —C≡C—, C=O, C=S, —C(=O)O—, —OC(=O)—, Si(R$^5$)$_2$, NR$^5$, —O— or —S—;
R$^3$, R$^4$ are on each occurrence, identically or differently, H, D, F, Cl, CN, or an alkyl, alkoxy or thioalkoxy group having 1 to 10 C atoms, which may be substituted by one or more radicals R$^5$, where one or more CH$_2$ groups in the alkyl, alkoxy or thioalkoxy groups may each be replaced by —R$^5$C=CR$^5$—, —C≡C—, C=O, C=S, —C(=O)O—, —OC(=O)—, Si(R$^5$)$_2$, NR$^5$, —O— or —S—;
R$^5$ is on each occurrence, identically or differently, H, D, F, Cl, CN, N(R$^6$)$_2$, an alkyl, alkoxy or thioalkoxy group having 1 to 10 C atoms or an alkenyl or alkynyl group having 2 to 20 C atoms, where the above-mentioned groups may each be substituted by one or more radicals R$^6$ and where one or more CH$_2$ groups in the above-mentioned groups may each be replaced by —R$^6$C=CR$^6$—, —C≡C—, C=O, C=S, —C(=O)O—, —O(C=O)—, Si(R$^6$)$_2$, NR$^6$, —O— or —S—, or an aryl or heteroaryl group having 5 to 30 aromatic ring atoms, which may in each case be substituted by one or more radicals R$^6$;
R$^6$ is on each occurrence, identically or differently, H, F or an aliphatic organic radical having 1 to 20 C atoms, in which one or more H atoms may be replaced by F, or an aryl or heteroaryl group having 5 to 20 C atoms, in which one or more H atoms may each be replaced by F;
i is equal to 0, 1, 2, 3, 4 or 5; and
wherein said switching layer further comprises a liquid-crystalline medium having a clearing point in the temperature range from 90° C. to 170° C., wherein said medium comprises one or more different compounds,
wherein said device is capable of regulating the passage of energy in the form of light emitted by the sun from the environment into an inside space, and
wherein said device is
(a) electrically switchable from a state having relatively low light transmissivity into a state having higher light transmissivity; or
(b) electrically switchable from a state having relatively high light transmissivity into a state having lower light transmissivity.

2. The device according to claim 1, wherein X is CR$^2$.
3. The device according to claim 1, wherein Y is S.
4. The device according to claim 1, wherein Z$^1$ is a single bond.
5. The device according to claim 1, wherein Z$^2$ stands on each occurrence, identically or differently, for a single bond, —C(R$^3$)$_2$C(R$^3$)$_2$—, —CR$^3$=CR$^3$—, —C≡C—, OC(R$^3$)$_2$— or —C(R$^3$)$_2$O—.
6. The device according to claim 1, wherein Ar$^1$ represents on each occurrence, identically or differently, an aryl group having 6 to 15 C atoms or a heteroaryl group having 5 to 15 C atoms, which may be substituted by one or more radicals R$^4$.
7. The device according to claim 1, wherein Ar$^1$ is on each occurrence, identically or differently, benzene, fluorene, naphthalene, pyridine, pyrimidine, pyrazine, triazine, thiophene, thiophene with condensed-on 1,4-dioxane ring, benzothiophene, dibenzothiophene, benzodithiophene, cyclopenta-dithiophene, thienothiophene, indenothiophene, dithienopyrrole, silolodithiophene, selenophene, benzoselenophene, dibenzoselenophene, furan, benzofuran, dibenzofuran, or quinoline, each of which is optionally substituted by radicals $R^4$.

8. The device according to claim 1, wherein at least one $Ar^1$ is selected from a sulfur-containing heteroaryl group, which may be substituted by one or more radicals $R^4$.

9. The device according to claim 1, wherein $R^1$ is on each occurrence, identically or differently, a straight-chain or branched alkyl or alkoxy group having 3 to 8 C atoms, which may be substituted by one or more radicals $R^5$, where one or more $CH_2$ groups in the alkyl and alkoxy groups may each be replaced by —O—, —S— or —$R^5C$=$CR^5$—, or a siloxanyl group having 1 to 6 Si atoms, which may be substituted by one or more radicals $R^5$.

10. The device according to claim 1, wherein i is 1 or 2.

11. The device according to claim 1, wherein the degree of anisotropy R of the compound of the formula (I) or formula (II) is greater than 0.4.

12. The device according to claim 1, wherein said device is connected to a solar cell or another device for conversion of light and/or heat energy into electrical energy.

13. A window comprising a device according to claim 1.

14. The device according to claim 1, wherein said one or more compounds of formula (I) or formula (II) are selected from compounds of formula (I).

15. The device according to claim 1, wherein said one or more or more dichroic dyes are selected from formula (IIa)

formula (IIa)

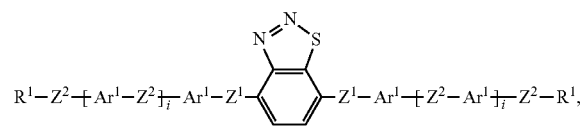

where:
Z$^1$ is on each occurrence, identically or differently, a single bond, —CR$^3$=CR$^3$— or —C≡C—;
Z$^2$ is on each occurrence, identically or differently, a single bond, O, S, C(R$^3$)$_2$, —CR$^3$=CR$^3$— or —C≡C—;
Ar$^1$ is on each occurrence, identically or differently, an aryl or heteroaryl group having 5 to 30 aromatic ring atoms, which may be substituted by one or more radicals R$^4$;
R$^1$ is on each occurrence, identically or differently, H, D, F, CN, N(R$^5$)$_2$, or an alkyl, alkoxy or thioalkoxy group having 1 to 10 C atoms, which may be substituted by one or more radicals R$^5$, where one or more CH$_2$ groups in the alkyl, alkoxy or thioalkoxy groups may be replaced by —R$^5$C=CR$^5$—, —C≡C—, C=O, C=S, —C(=O)O—, —OC(=O)—, Si(R$^5$)$_2$, NR$^5$, —O— or —S—;

R$^2$ is on each occurrence, identically or differently, N(R$^5$)$_2$ or a straight-chain or branched alkyl or alkoxy having 3 to 10 H C atoms, which may be substituted by one or more radicals R$^5$, where one or more CH$_2$ groups in the alkyl, alkoxy or thioalkoxy groups may each be replaced by —O—, —S—, —R$^5$C=CR$^5$—, or a siloxanyl group having 1 to 10 Si atoms, which may be substituted by one or more radicals R$^5$;

R$^3$, R$^4$ are on each occurrence, identically or differently, H, D, F, Cl, CN, or an alkyl, alkoxy or thioalkoxy group having 1 to 10 C atoms, which may be substituted by one or more radicals R$^5$, where one or more CH$_2$ groups in the alkyl, alkoxy or thioalkoxy groups may each be replaced by —R$^5$C=CR$^5$—, —C≡C—, C=O, C=S, —C(=O)O—, —OC(=O)—, Si(R$^5$)$_2$, NR$^5$, —O— or —S—;

R$^5$ is on each occurrence, identically or differently, H, D, F, Cl, CN, N(R$^6$)$_2$, an alkyl, alkoxy or thioalkoxy group having 1 to 10 C atoms or an alkenyl or alkynyl group having 2 to 20 C atoms, where the above-mentioned groups may each be substituted by one or more radicals R$^6$ and where one or more CH$_2$ groups in the above-mentioned groups may each be replaced by —R$^6$C=CR$^6$—, —C≡C—, C=O, C=S, —C(=O)O—, —O(C=O)—, Si(R$^6$)$_2$, NR$^6$, —O— or —S—, or an aryl or heteroaryl group having 5 to 30 aromatic ring atoms, which may in each case be substituted by one or more radicals R$^6$;

R$^6$ is on each occurrence, identically or differently, H, F or an aliphatic organic radical having 1 to 20 C atoms, in which one or more H atoms may be replaced by F, or an aryl or heteroaryl group having 5 to 20 C atoms, in which one or more H atoms may each be replaced by F;

i is equal to 0, 1, 2, 3, 4 or 5.

16. The device according to claim 15, wherein Ar$^1$ is on each occurrence, identically or differently, benzene, fluorene, naphthalene, pyridine, pyrimidine, pyrazine, triazine, thiophene, thiophene with condensed-on 1,4-dioxane ring, benzothiophene, dibenzothiophene, benzodithiophene, cyclopentadithiophene, thienothiophene, indenothiophene, dithienopyrrole, silolo-dithiophene, selenophene, benzoselenophene, dibenzoselenophene, furan, benzo-furan, dibenzofuran or quinoline, each of which is optionally substituted by radicals R$^4$.

17. The device according to claim 15, wherein R$^1$ is on each occurrence, identically or differently, a straight-chain or branched alkyl or alkoxy group having 3 to 8 C atoms, which may be substituted by one or more radicals R$^5$, where one or more CH$_2$ groups in the alkyl and alkoxy groups may each be replaced by —O—, —S— or —R$^5$C=CR$^5$—, or a siloxanyl group having 1 to 6 Si atoms, which may be substituted by one or more radicals R$^5$.

18. The device according to claim 1, wherein said one or more compounds of formula (I) or formula (II) are in each case selected from the group consisting of:

(1) 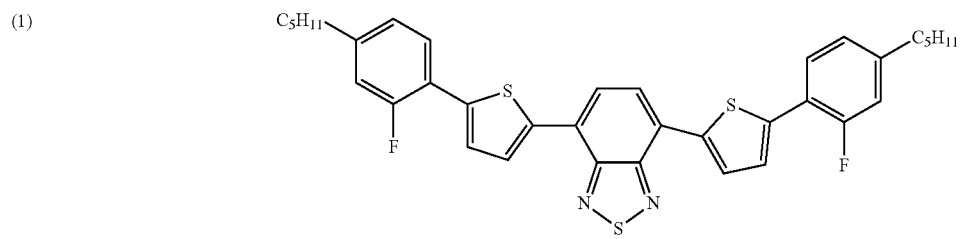
(2) 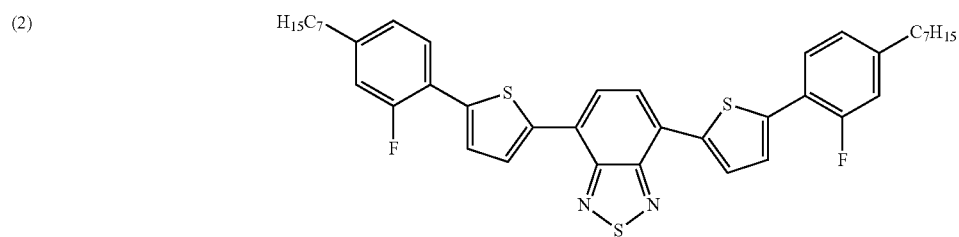
(4) 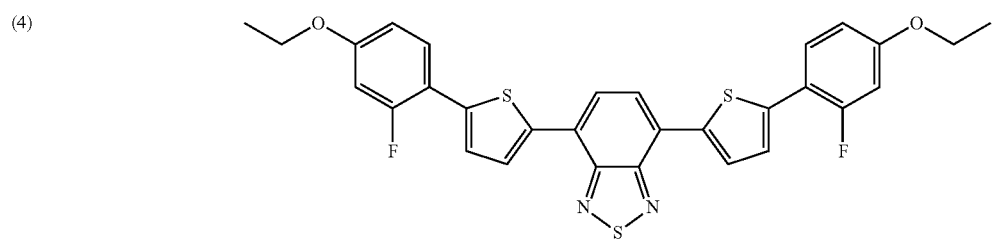
(5) 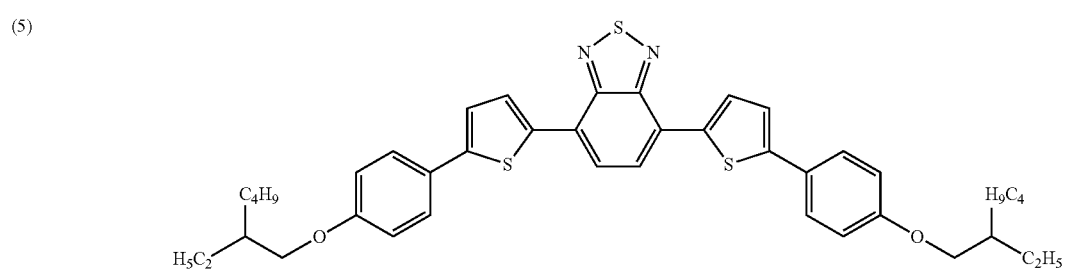
(6) 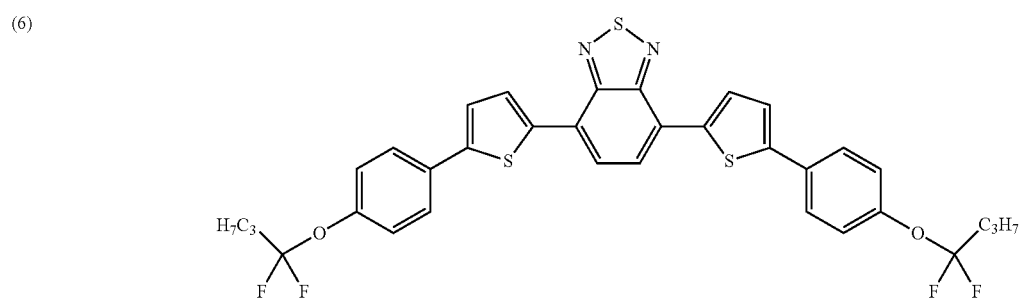
(7) 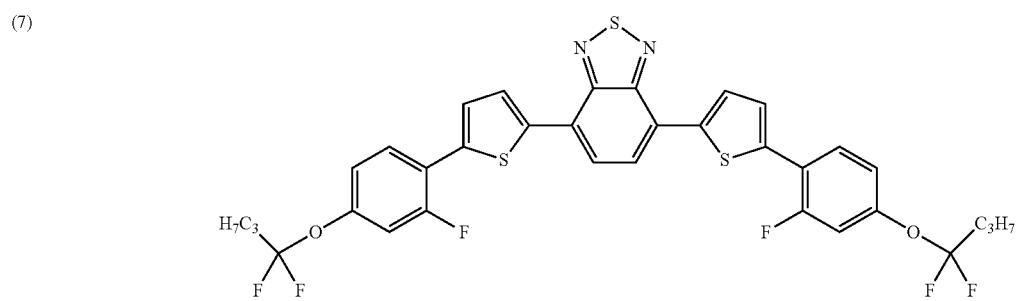

(10) 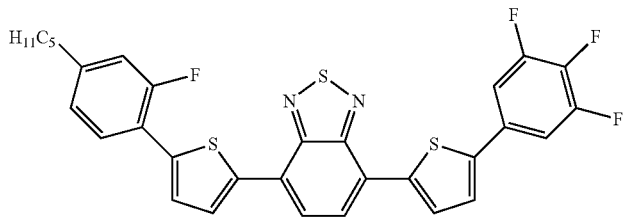
(11) 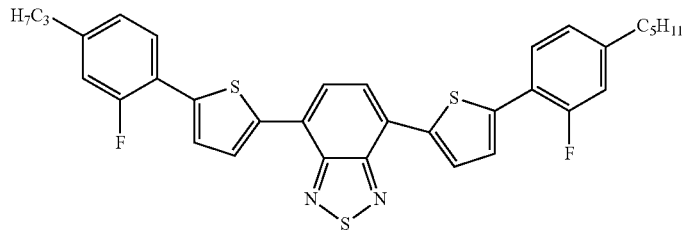
(12) 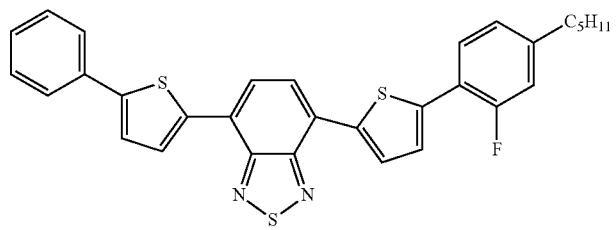
(13) 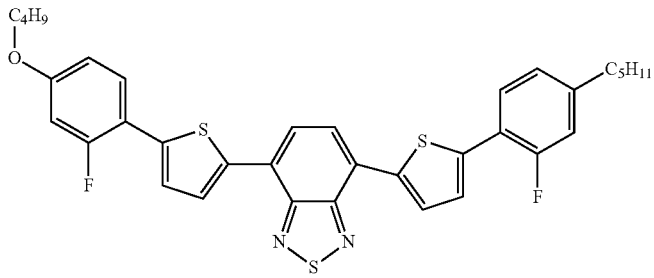
(14) 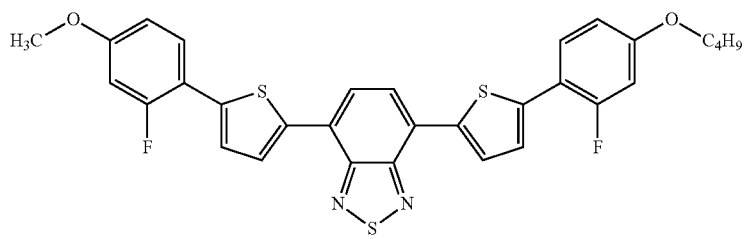
(15) 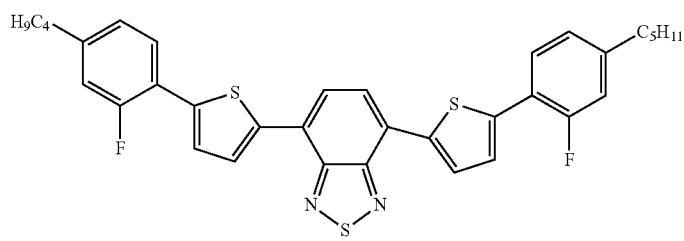

-continued
(16)
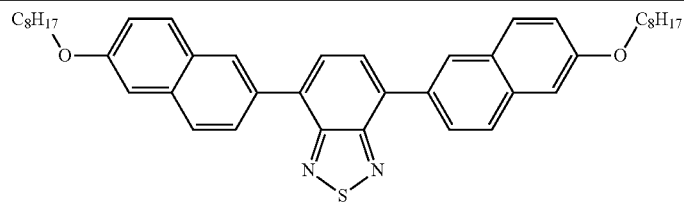
(17)
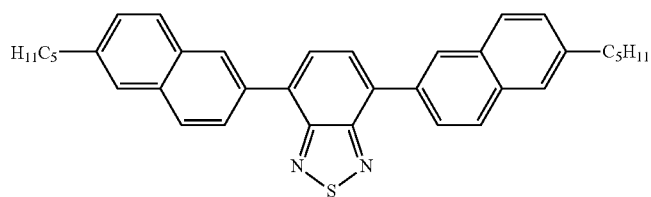
(19)
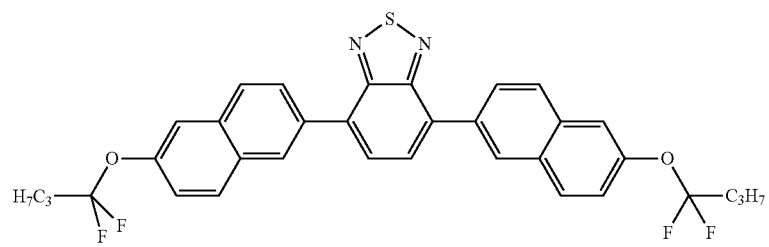
(20)
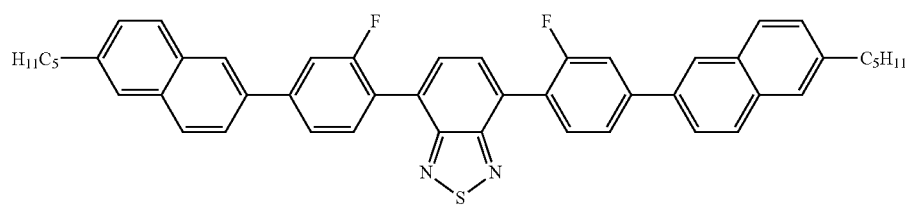
(21)
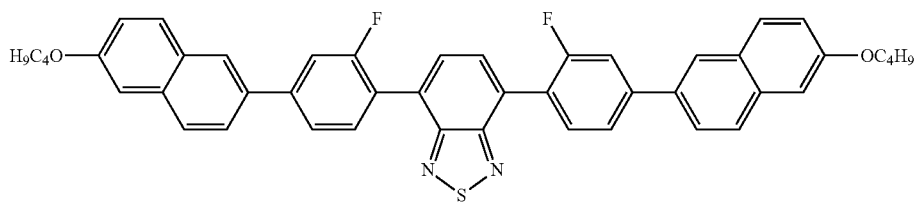
(24)
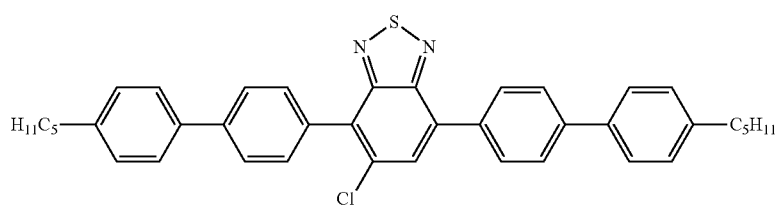
(25)
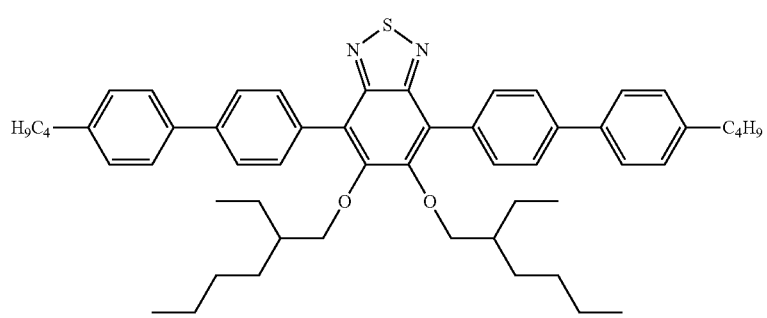

(26) 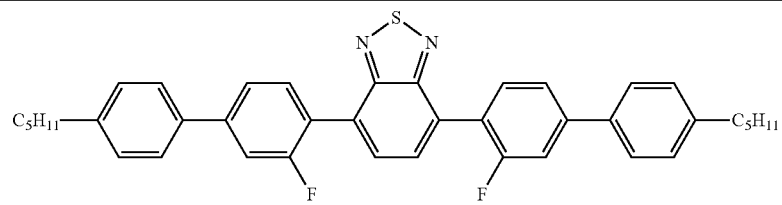
(27) 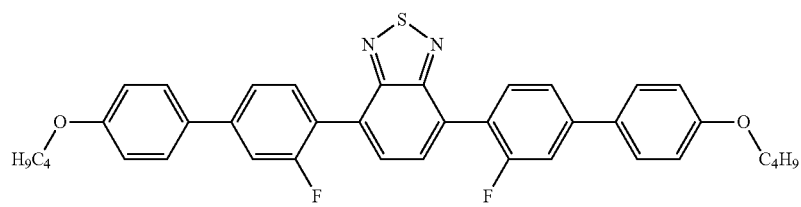
(28) 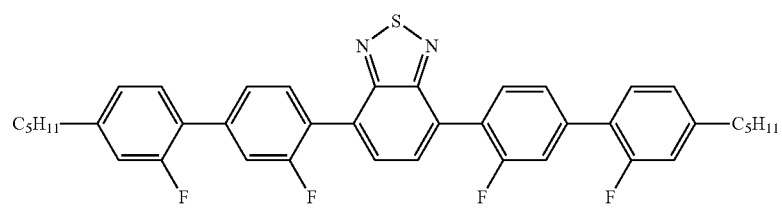
(29) 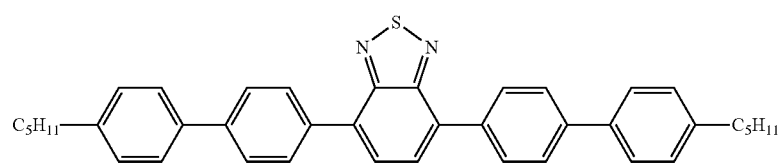
(30) 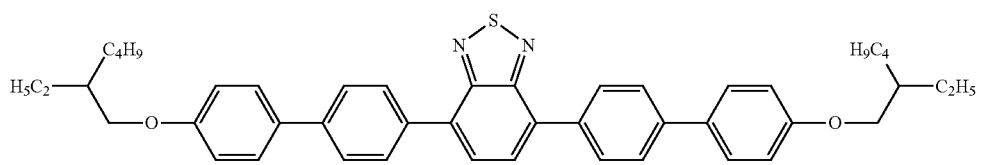
(31) 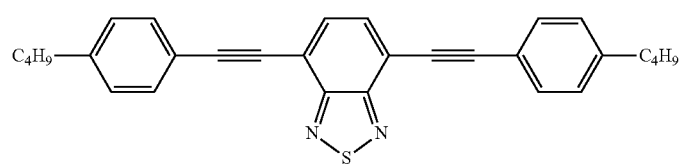
(32) 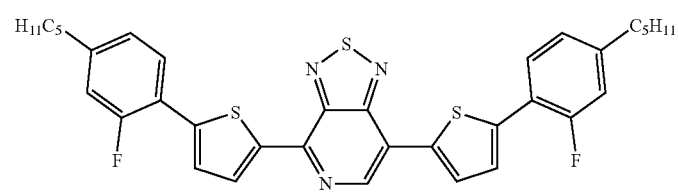
(33) 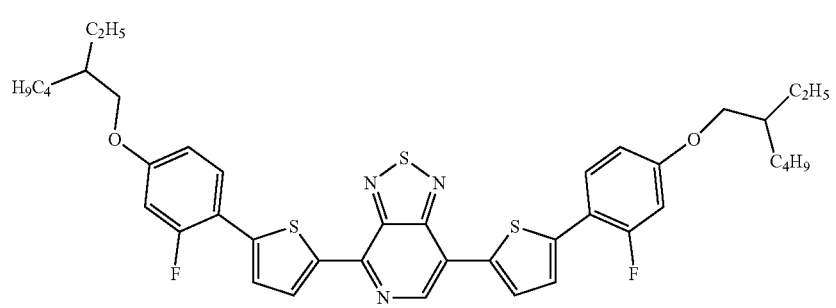

-continued
(34)
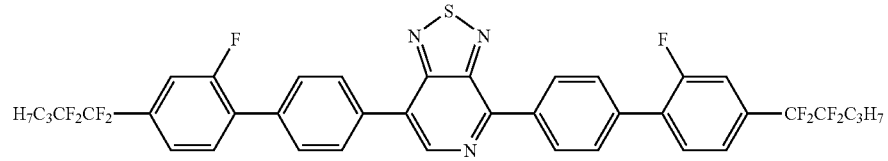
(35)
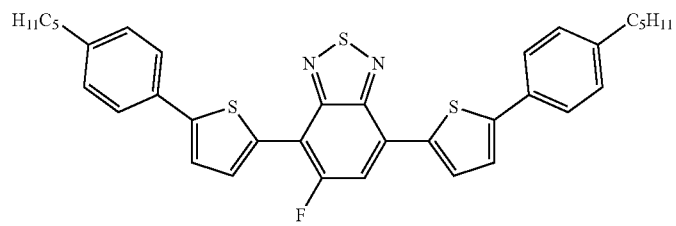
(36)
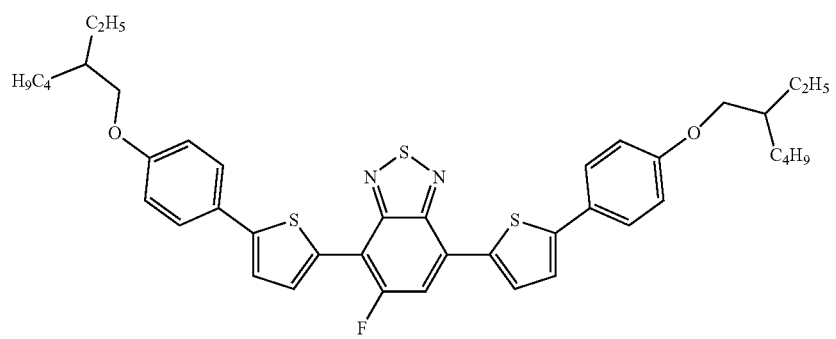
(37)
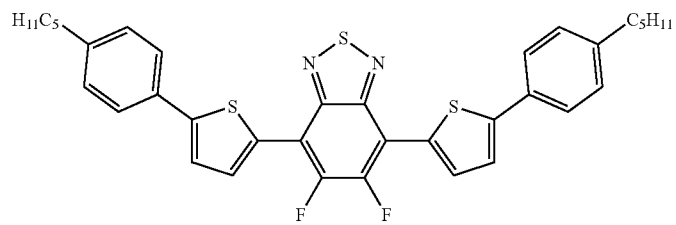
(38)
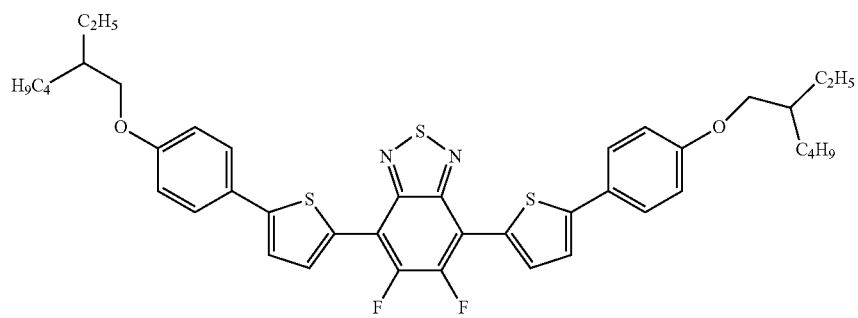
(39)
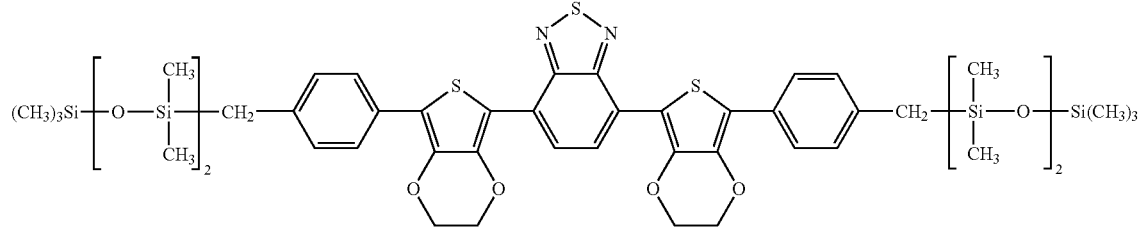

-continued
(40)
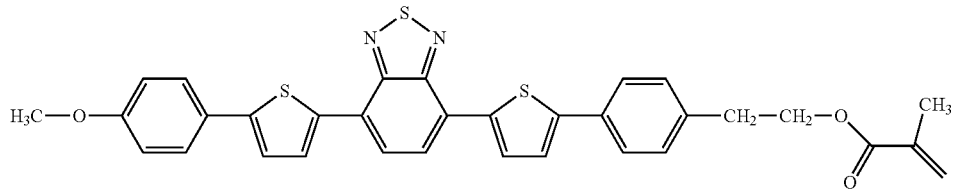 [SMILES: C=C(C)C(=O)OCCc1ccc(-c2ccc(-c3ccc(-c4ccc(-c5ccc(OC)cc5)s4)c4nsnc34)s2)cc1]
(41)
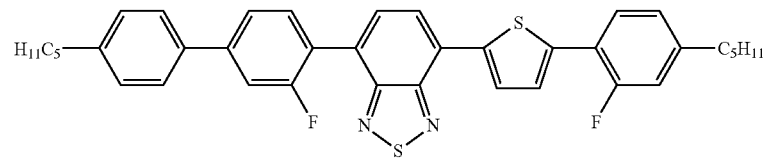
(42)
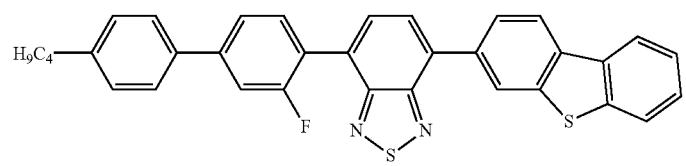
(43)
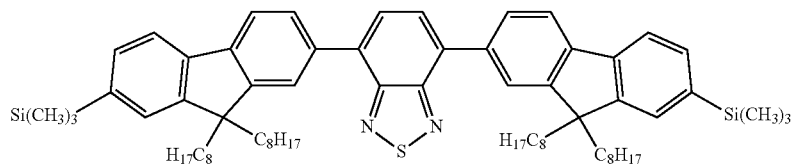
(44)
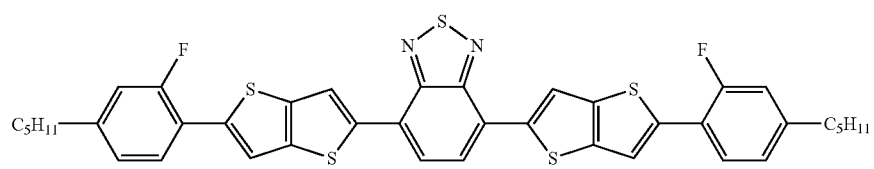
(45)
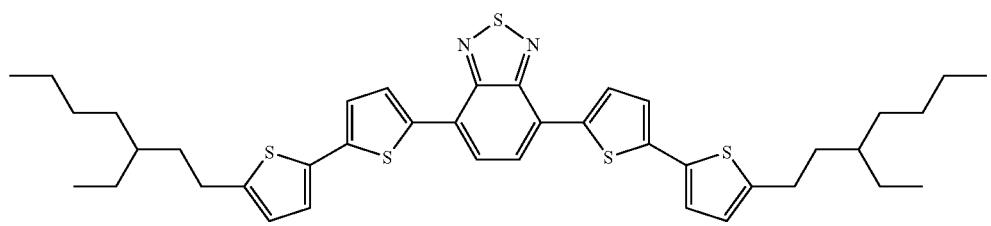 [SMILES: CCCCC(CC)CCc1ccc(-c2ccc(-c3ccc(-c4ccc(-c5ccc(CCC(CC)CCCC)s5)s4)c4nsnc34)s2)s1]
(46)
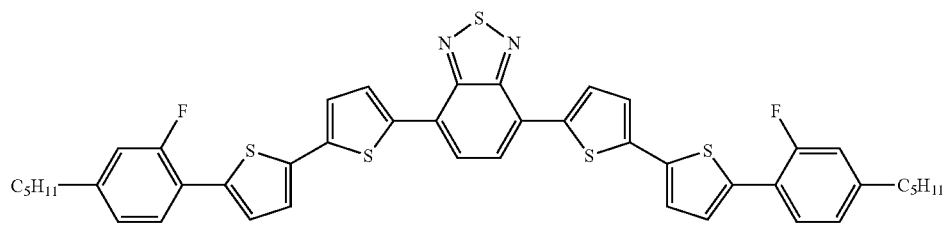
(47)
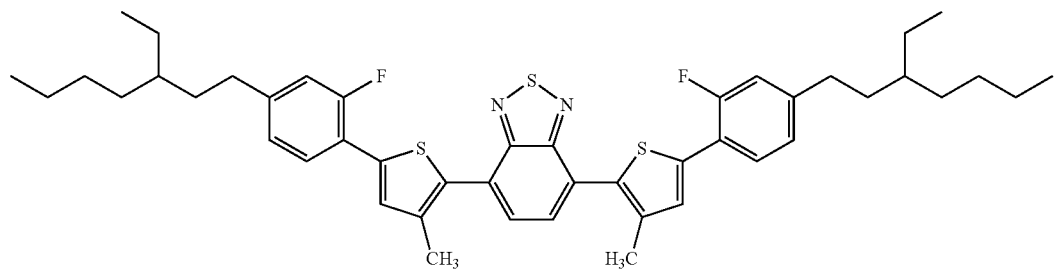 [SMILES: CCCCC(CC)CCc1ccc(-c2cc(C)c(-c3ccc(-c4sc(-c5ccc(CCC(CC)CCCC)cc5F)cc4C)c4nsnc34)s2)c(F)c1]

(48) 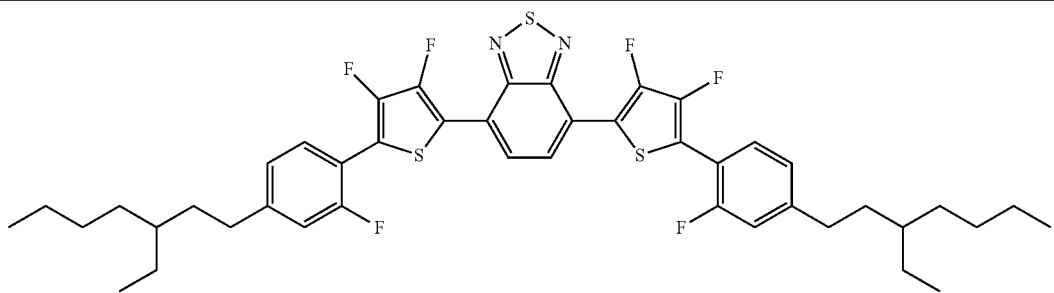
(49) 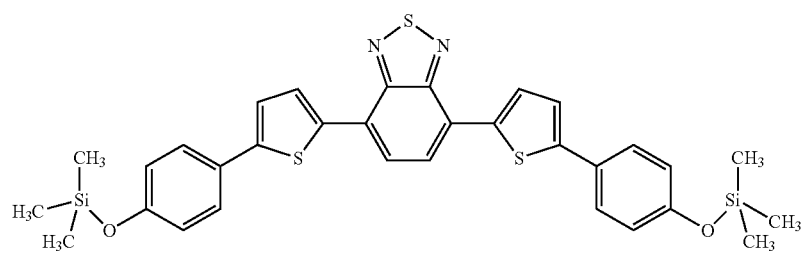
(50) 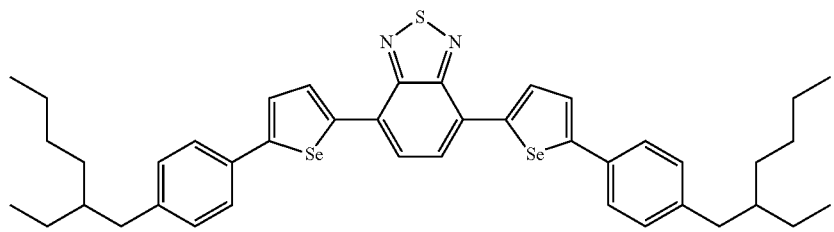 [SMILES: CCCCC(CC)Cc1ccc(-c2ccc(-c3ccc(-c4ccc(-c5ccc(CC(CC)CCCC)cc5)[se]4)c4nsnc34)[se]2)cc1]
(51) 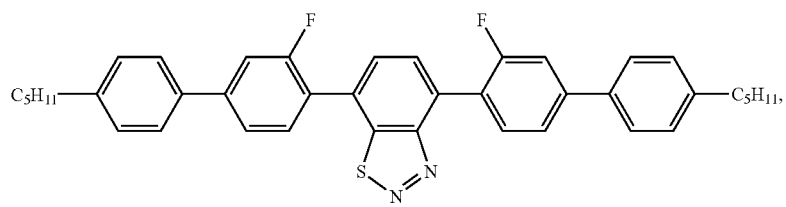
and
(52) 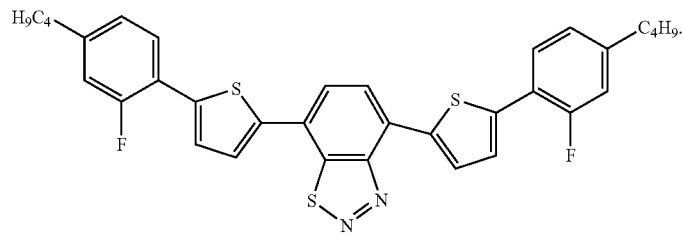
19. The device according to claim 1, wherein said one or more dichroic dyes are of the formulae (I-2-2), (I-2-3) or (I-2-4):
formula (I-2-2)
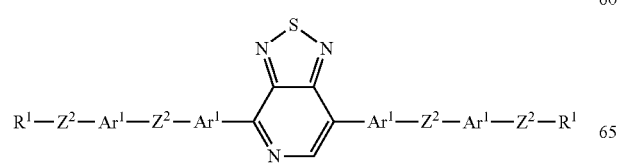

formula (I-2-3)

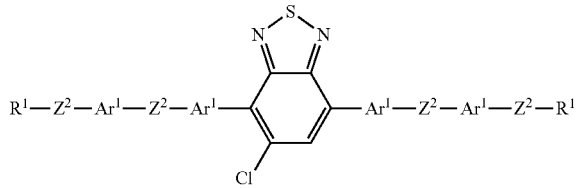

formula (I-2-4)

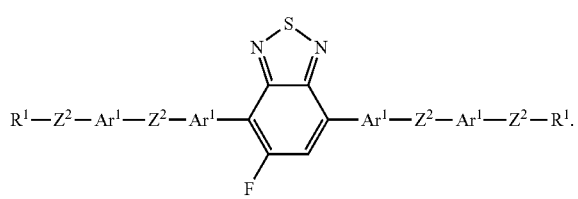

20. The device according to claim 1, wherein i is 2, 3, 4 or 5.

21. The device according to claim 1, wherein the liquid-crystalline medium of the switching layer has a clearing point in the temperature range from 95° C. to 170° C.

22. The device according to claim 1, wherein the liquid-crystalline medium of the switching layer has a clearing point in the temperature range from 105° C. to 170° C.

23. The device according to claim 1, wherein said device is electrically switchable from a state having relatively low light transmissivity, which is present without voltage, into a state having higher light transmissivity, wherein said liquid-crystalline medium of the switching layer is nematic in both states.

24. The device according to claim 1, wherein said device is electrically switchable from a state having relatively high light transmissivity, which is present without voltage, into a state having lower light transmissivity, wherein said liquid-crystalline medium of the switching layer is nematic in both states.

* * * * *